US011124827B2

(12) United States Patent
Bajaj

(10) Patent No.: US 11,124,827 B2
(45) Date of Patent: Sep. 21, 2021

(54) PERIOD-TO-PERIOD ANALYSIS OF AC SIGNALS FROM NANOPORE SEQUENCING

(71) Applicant: Roche Sequencing Solutions, Inc., Pleasanton, CA (US)

(72) Inventor: Kapil M. S. Bajaj, Newark, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 1044 days.

(21) Appl. No.: 15/628,353

(22) Filed: Jun. 20, 2017

(65) Prior Publication Data

US 2017/0370902 A1 Dec. 28, 2017

Related U.S. Application Data

(60) Provisional application No. 62/354,106, filed on Jun. 23, 2016.

(51) Int. Cl.
*C12Q 1/6869* (2018.01)
*G01N 33/487* (2006.01)
*G01N 27/327* (2006.01)

(52) U.S. Cl.
CPC ..... *C12Q 1/6869* (2013.01); *G01N 33/48721* (2013.01); *G01N 27/3278* (2013.01)

(58) Field of Classification Search
None
See application file for complete search history.

(56) References Cited

U.S. PATENT DOCUMENTS

| 5,733,729 | A | 3/1998 | Lipshutz et al. |
| 5,853,979 | A | 12/1998 | Green et al. |
| 6,066,454 | A | 5/2000 | Lipshutz et al. |
| 6,228,593 | B1 | 5/2001 | Lipshutz et al. |
| 6,546,340 | B2 | 4/2003 | Lipshutz et al. |
| 6,957,149 | B2 | 10/2005 | Lipshutz et al. |
| 7,039,238 | B2 | 5/2006 | Sonmez et al. |
| 7,133,781 | B2 | 11/2006 | Toll et al. |
| 7,617,054 | B2 | 11/2009 | Sayer et al. |
| 8,126,235 | B2 | 2/2012 | Shi et al. |
| 8,182,993 | B2 | 5/2012 | Tomaney et al. |
| 8,200,648 | B2 | 6/2012 | Boiman et al. |
| 8,370,079 | B2 | 2/2013 | Sorenson et al. |
| 8,428,886 | B2 | 4/2013 | Wong et al. |
| 8,645,343 | B2 | 2/2014 | Wong et al. |
| 8,703,422 | B2 | 4/2014 | Tomaney et al. |
| 9,165,109 | B2 | 10/2015 | Chaisson |
| 9,175,343 | B2 | 11/2015 | Tomaney et al. |
| 9,194,838 | B2 | 11/2015 | Taniguchi et al. |
| 9,218,451 | B2 | 12/2015 | Wong et al. |
| 9,395,353 | B2 | 7/2016 | Gu et al. |
| 9,546,400 | B2 | 1/2017 | Turner et al. |
| 9,574,228 | B2 | 2/2017 | Gu et al. |
| 2009/0012766 | A1 | 1/2009 | Miyake et al. |
| 2010/0122907 | A1 | 5/2010 | Stanford et al. |
| 2012/0173159 | A1 | 7/2012 | Davey et al. |
| 2013/0060482 | A1 | 3/2013 | Sikora et al. |
| 2013/0090860 | A1 | 4/2013 | Sikora et al. |
| 2013/0146456 | A1 | 6/2013 | Gundlach et al. |
| 2013/0217006 | A1 | 8/2013 | Sorenson et al. |
| 2013/0274148 | A1 | 10/2013 | Kain et al. |
| 2014/0051068 | A1 | 2/2014 | Cherf et al. |
| 2014/0134616 | A1 | 5/2014 | Davis et al. |
| 2015/0060276 | A1 | 3/2015 | Golovchenko et al. |
| 2015/0107996 | A1 | 4/2015 | Chen |
| 2015/0111759 | A1 | 4/2015 | Ju et al. |
| 2015/0119259 | A1 | 4/2015 | Ju et al. |
| 2015/0169824 | A1 | 6/2015 | Kermani et al. |
| 2015/0193431 | A1 | 7/2015 | Stoytchev et al. |
| 2015/0344945 | A1 | 12/2015 | Mandell et al. |
| 2016/0097093 | A1 | 4/2016 | Tomaney et al. |
| 2016/0110499 | A1 | 4/2016 | Donnet |
| 2016/0138101 | A1 | 5/2016 | Taniguchi et al. |
| 2016/0162634 | A1 | 6/2016 | Reid et al. |
| 2017/0002403 | A1 | 1/2017 | Gu et al. |
| 2017/0089858 | A1 | 3/2017 | Fernandez-Gomez et al. |

(Continued)

FOREIGN PATENT DOCUMENTS

| CN | 102621214 | 11/2001 |
| CN | 104066850 | 10/2003 |

(Continued)

OTHER PUBLICATIONS

International Search Report dated Aug. 30, 2017 and the Written Opinion of the International Searching Authority corresponding to International Application PCT/EP2017/065423 (eleven pages).

(Continued)

*Primary Examiner* — G Steven Vanni

(74) *Attorney, Agent, or Firm* — Kilpatrick Townsend and Stockton LLP

(57) ABSTRACT

An alternating signal is applied across a nanopore of a sequencing cell, the nanopore being configured to receive a tag that is connected to a nucleotide, thereby creating a threading event. A first set of voltage data is acquired during a first portion of a plurality of cycles of the alternating signal. Each data point of the first set of voltage data corresponds to a value of a resistance of the nanopore at a different time, where the resistance of the nanopore changes when the tag is received within the nanopore. A shifted set of voltage data is determined from the first set of voltage data and difference data is computed by computing differences between data points of the first set of voltage data and corresponding data points of the shifted set of voltage data. Threading events may be identified based on the difference data.

21 Claims, 15 Drawing Sheets

(56) References Cited

U.S. PATENT DOCUMENTS

| | | |
|---|---|---|
| 2017/0091427 A1 | 3/2017 | Massingham |
| 2017/0096703 A1 | 4/2017 | Dolan et al. |
| 2017/0154036 A9 | 6/2017 | Stoytchev et al. |
| 2017/0219557 A1 | 8/2017 | Reid et al. |

FOREIGN PATENT DOCUMENTS

| | | |
|---|---|---|
| CN | 102834527 | 2/2008 |
| CN | 102899243 | 10/2008 |
| CN | 104955958 | 1/2010 |
| CN | 103392008 | 8/2011 |
| EP | 0835442 B1 | 3/1999 |
| EP | 2758545 B1 | 7/2017 |
| JP | 2003531592 | 7/2010 |
| JP | 2010501077 | 8/2012 |
| JP | 2010524436 | 12/2012 |
| JP | 2014174022 | 1/2013 |
| JP | 58223927 | 11/2013 |
| JP | 2016095314 | 9/2014 |
| WO | 2008124107 | 12/1983 |
| WO | 2013/041878 A1 | 3/2013 |
| WO | 0181908 | 9/2014 |
| WO | 2008021488 | 9/2015 |
| WO | 2016/023010 A1 | 2/2016 |
| WO | 2011097028 | 5/2016 |

OTHER PUBLICATIONS

International Search Report and Written Opinion from PCT Application PCT/EP2018/085734 dated Apr. 18, 2019; 13 pages.

Wang, Y. et al.; "The evolution of nanopore sequencing"; *Frontiers in Genetics*; vol. 5, No. 449; Jan. 7, 2015; pp. 1-20.

PERIOD-TO-PERIOD ANALYSIS OF AC SIGNALS FROM NANOPORE SEQUENCING

CROSS-REFERENCES TO RELATED APPLICATIONS

This application claims priority to U.S. Provisional Patent Application 62/354,106 filed Jun. 23, 2016, the disclosure of which is incorporated by reference in its entirety for all purposes.

BACKGROUND

Nanopore membrane devices having pore sizes on the order of one nanometer in internal diameter have shown promise in rapid nucleotide sequencing. When a voltage signal is applied across a nanopore immersed in a conducting fluid, the electric field can move ions in the conducting fluid through the nanopore. The movement of ions in the conducting fluid through the nanopore can cause a small ion current. The voltage applied can also move the molecules to be sequenced into, through, or out of the nanopore. The level of the ion current (or a corresponding voltage) depends on the sizes and chemical structures of the nanopore and the particular molecule that has been moved into the nanopore.

As an alternative to a DNA molecule (or other nucleic acid molecule to be sequenced) moving through the nanopore, a molecule (e.g., a nucleotide being added to a DNA strand) can include a particular tag of a particular size and/or structure. The ion current or a voltage in a circuit including the nanopore (e.g., at an integrating capacitor) can be measured as a way of measuring the resistance of the nanopore corresponding to the molecule, thereby allowing the detection of the particular molecule in the nanopore, and the particular nucleotide at a particular position of a nucleic acid.

A nanopore based sequencing chip may be used for DNA sequencing. A nanopore based sequencing chip can incorporate a large number of sensor cells configured as an array. For example, an array of one million cells may include 1000 rows by 1000 columns of cells.

The voltages that are measured can vary from chip to chip and from cell to cell of a same chip due to manufacturing variability. Therefore, it can be difficult to determine the correct molecule, which may be or correspond to the correct nucleotide in a particular nucleic acid or other polymer in a cell.

Accordingly, improved techniques are desired for sequencing.

BRIEF SUMMARY

Embodiments can provide systems, methods, and apparatuses for signal-processing and base-calling for primary analysis of nanopore sequencing using an AC waveform applied to the nanopore. A differencing technique can be used.

In some embodiments, a differencing scheme can be 1-period or n-periods based. It is also possible to do multiple differencing schemes for locating events in time, where an event can correspond to a nucleotide being added to a nucleic acid, as may be detected with a tag attached to the nucleotide moving into the nanopore. Different measures like time-to-thread (TTT), dwell times, etc. can be obtained.

Other embodiments are directed to systems, portable consumer devices, and computer readable media associated with methods described herein.

A better understanding of the nature and advantages of embodiments of the present invention may be gained with reference to the following detailed description and the accompanying drawings.

TERMS

Figure 1:
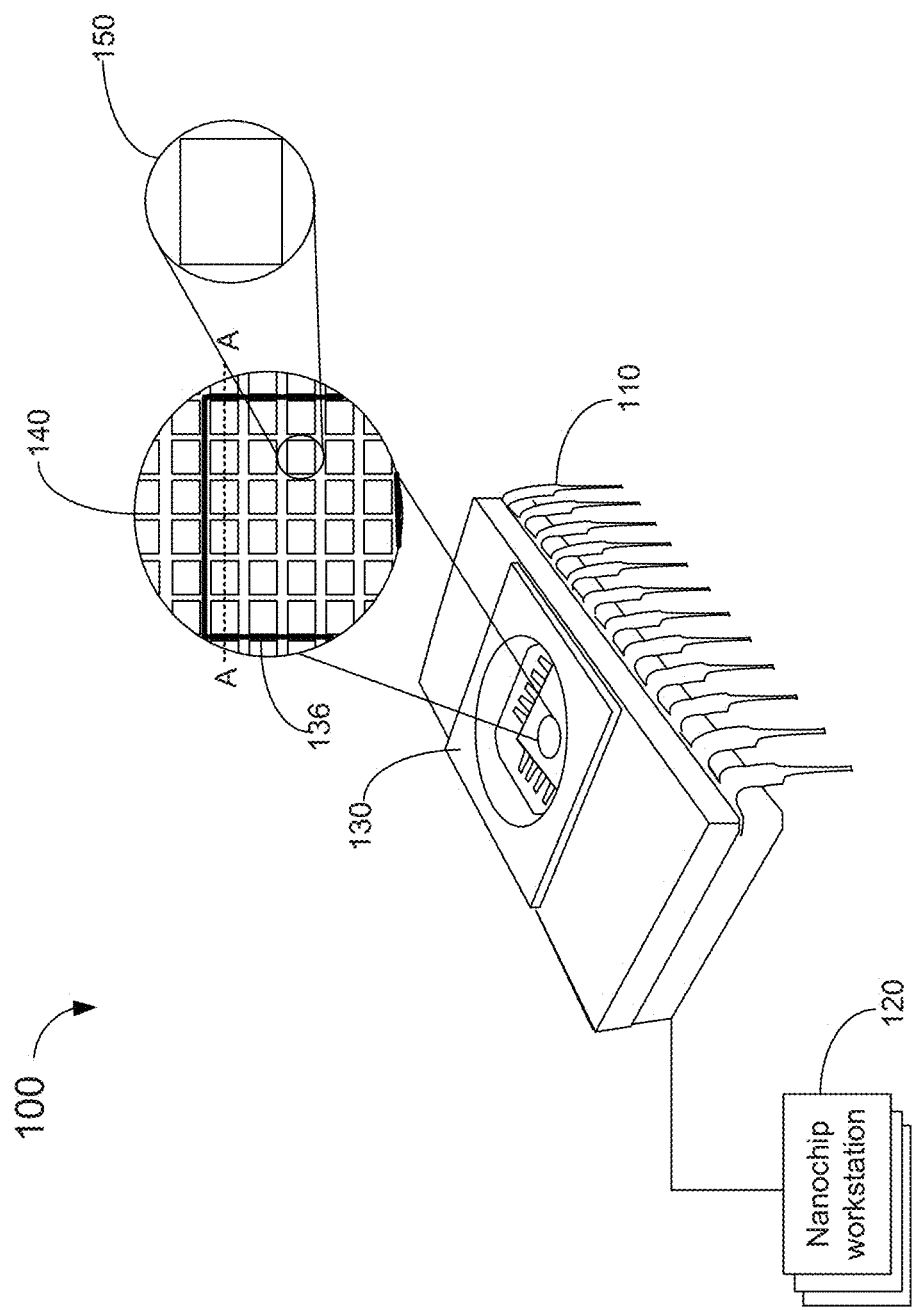
FIG. 1 is a top view of an embodiment of a nanopore sensor chip having an array of nanopore cells.

Unless defined otherwise, technical and scientific terms used herein have the same meaning as commonly understood by a person of ordinary skill in the art. Methods, devices, and materials similar or equivalent to those described herein can be used in the practice of disclosed techniques. The following terms are provided to facilitate understanding of certain terms used frequently and are not meant to limit the scope of the present disclosure. Abbreviations used herein have their conventional meaning within the chemical and biological arts.

"Nucleic acid" may refer to deoxyribonucleotides or ribonucleotides and polymers thereof in either single- or double-stranded form. The term may encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs may include, without limitation, phosphorothioates, phosphoramidites, methyl phosphonates, chiral-methyl phosphonates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid may be used interchangeably with gene, cDNA, mRNA, oligonucleotide, and polynucleotide.

The term "template" may refer to a single stranded nucleic acid molecule that is copied into a complementary strand of DNA nucleotides for DNA synthesis. In some cases, a template may refer to the sequence of DNA that is copied during the synthesis of mRNA.

The term "primer" may refer to a short nucleic acid sequence that provides a starting point for DNA synthesis. Enzymes that catalyze the DNA synthesis, such as DNA polymerases, can add new nucleotides to a primer for DNA replication.

"Polymerase" refers to an enzyme that performs template-directed synthesis of polynucleotides. The term encompasses both a full length polypeptide and a domain that has polymerase activity. DNA polymerases are well-known to those skilled in the art, and include but are not limited to DNA polymerases isolated or derived from *Pyrococcus furiosus, Thermococcus litoralis*, and *Thermotoga maritime*, or modified versions thereof. They include both DNA-dependent polymerases and RNA-dependent polymerases such as reverse transcriptase. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

"Nanopore" refers to a pore, channel or passage formed or otherwise provided in a membrane. A membrane can be an organic membrane, such as a lipid bilayer, or a synthetic membrane, such as a membrane formed of a polymeric material. The nanopore can be disposed adjacent or in proximity to a sensing circuit or an electrode coupled to a sensing circuit, such as, for example, a complementary metal oxide semiconductor (CMOS) or field effect transistor (FET) circuit. In some examples, a nanopore has a characteristic width or diameter on the order of 0.1 nanometers (nm) to about 1000 nm. Some nanopores are proteins.

"Nucleotide," in addition to referring to the naturally occurring ribonucleotide or deoxyribonucleotide monomers, can be understood to refer to related structural variants thereof, including derivatives and analogs, that are functionally equivalent with respect to the particular context in which the nucleotide is being used (e.g., hybridization to a complementary base), unless the context clearly indicates otherwise.

"Tag" refers to a detectable moiety that can be atoms or molecules, or a collection of atoms or molecules. A tag can provide an optical, electrochemical, magnetic, or electrostatic (e.g., inductive, capacitive) signature, which signature may be detected with the aid of a nanopore. Typically, when a nucleotide is attached to the tag it is called a "Tagged Nucleotide." The tag can be attached to the nucleotide via the phosphate moiety.

As used herein, the term "bright period" may generally refer to the time period when a tag of a tagged nucleotide is forced into a nanopore by an electric field applied through an AC signal. The term "dark period" may generally refer to the time period when a tag of a tagged nucleotide is pushed out of the nanopore by the electric field applied through the AC signal. An AC cycle may include the bright period and the dark period. In different embodiments, the polarity of the voltage signal applied to a nanopore cell to put the nanopore cell into the bright period (or the dark period) may be different.

DETAILED DESCRIPTION

Certain methods of primary-analysis use a large number of parameters for signal processing of AC data (resulting from application of an alternating voltage) and base-calling for processed data generated by nanopore sequencing, where an AC signal is applied to the nanopore. Using a large number of parameters can be slow, noisy, and non-robust due to having large number of parameters, particularly when first applied to new system. Such filtering can also introduce its own artifacts (depending on filter(s) used and their parameters), can amplify noise and propagate errors to base-calling and alignment. The performance (speed, sensitivity, accuracy etc.) of primary-analysis is important.

In some embodiments, differences are determined between corresponding voltage measurements for a cycle of the AC data, and the difference data is analyzed to identify threading events of a tag in the nanopore, where the tag corresponds to a particular nucleotide. Some advantages can include: it is simple, fast, robust (does not require many or any external parameters), does not need any filtering, can also be easily implemented in FPGA and GPU, and can successfully eliminate most noise (other than ADC-noise). In addition, subsequent base-calling can be done on integrated data making it less sensitive to noise. Since embodiments can use a differencing of corresponding points from adjacent or otherwise nearby cycles (also referred to herein as local neighborhood), embodiment can be adaptive to local systematic variations in the raw data, e.g., correct for gain drift baseline shift or the like.

I. Nanopore Based Sequencing Chip

FIG. 1 is a top view of an embodiment of a nanopore sensor chip 100 having an array 140 of nanopore cells 150. Each nanopore cell 150 includes a control circuit integrated on a silicon substrate of nanopore sensor chip 100. In some embodiments, side walls 136 may be included in array 140 to separate groups of nanopore cells 150 so that each group may receive a different sample for characterization. Each nanopore cell may be used to sequence a nucleic acid. In some embodiments, nanopore sensor chip 100 may include a cover plate 130. In some embodiments, nanopore sensor chip 100 may also include a plurality of pins 110 for interfacing with other circuits, such as a computer processor.

In some embodiments, nanopore sensor chip 100 may include multiple chips in a same package, such as, for example, a Multi-Chip Module (MCM) or System-in-Package (SiP). The chips may include, for example, a memory, a processor, a field-programmable gate array (FPGA), an application-specific integrated circuit (ASIC), data converters, a high-speed I/O interface, etc.

In some embodiments, nanopore sensor chip 100 may be coupled to (e.g., docked to) a nanochip workstation 120, which may include various components for carrying out (e.g., automatically carrying out) various embodiments of the processes disclosed herein, including, for example, analyte delivery mechanisms, such as pipettes for delivering lipid suspension or other membrane structure suspension, analyte solution, and/or other liquids, suspension or solids, robotic arms, computer processor, and/or memory. A plurality of polynucleotides may be detected on array 140 of nanopore cells 150. In some embodiments, each nanopore cell 150 can be individually addressable.

II. Nanopore Sequencing Cell

Nanopore cells 150 in nanopore sensor chip 100 may be implemented in many different ways. For example, in some embodiments, tags of different sizes and/or chemical structures may be attached to different nucleotides in a nucleic acid molecule to be sequenced. In some embodiments, a complementary strand to a template of the nucleic acid molecule to be sequenced may be synthesized by hybridizing differently polymer-tagged nucleotides with the template. In some implementations, the nucleic acid molecule and the attached tags may both move through the nanopore, and an ion current passing through the nanopore may indicate the nucleotide that is in the nanopore because of the particular size and/or structure of the tag attached to the nucleotide. In some implementations, only the tags may be moved into the nanopore. There may also be many different ways to detect the different tags in the nanopores.

A. Nanopore Sequencing Cell Structure

Figure 2:
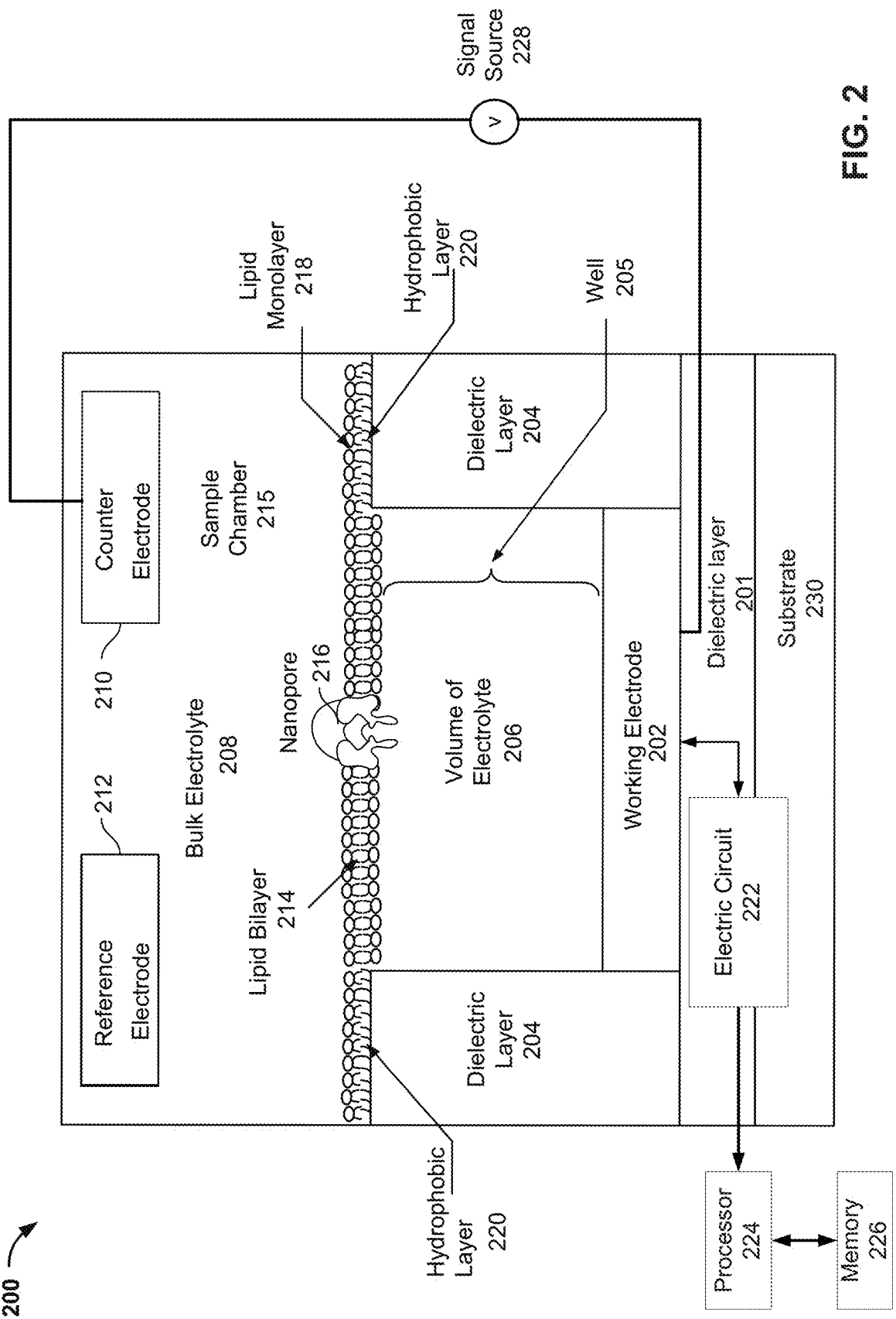
FIG. 2 illustrates an embodiment of a nanopore cell in a nanopore sensor chip that can be used to characterize a polynucleotide or a polypeptide.

FIG. 2 illustrates an embodiment of an example nanopore cell 200 in a nanopore sensor chip, such as nanopore cell 150 in nanopore sensor chip 100 of FIG. 1, that can be used to characterize a polynucleotide or a polypeptide. Nanopore cell 200 may include a well 205 formed of dielectric layers 201 and 204; a membrane, such as a lipid bilayer 214 formed over well 205; and a sample chamber 215 on lipid bilayer 214 and separated from well 205 by lipid bilayer 214. Well 205 may contain a volume of electrolyte 206, and sample chamber 215 may hold bulk electrolyte 208 containing a nanopore, e.g., a soluble protein nanopore transmembrane molecular complexes (PNTMC), and the analyte of interest (e.g., a nucleic acid molecule to be sequenced).

Nanopore cell 200 may include a working electrode 202 at the bottom of well 205 and a counter electrode 210 disposed in sample chamber 215. A signal source 228 may apply a voltage signal between working electrode 202 and counter electrode 210. A single nanopore (e.g., a PNTMC) may be inserted into lipid bilayer 214 by an electroporation process caused by the voltage signal, thereby forming a nanopore 216 in lipid bilayer 214. The individual membranes (e.g., lipid bilayers 214 or other membrane structures) in the array may be neither chemically nor electrically connected to each other. Thus, each nanopore cell in the array may be an independent sequencing machine, producing data unique to the single polymer molecule associated with the nanopore that operates on the analyte of interest and modulates the ionic current through the otherwise impermeable lipid bilayer.

As shown in FIG. 2, nanopore cell 200 may be formed on a substrate 230, such as a silicon substrate. Dielectric layer 201 may be formed on substrate 230. Dielectric material used to form dielectric layer 201 may include, for example, glass, oxides, nitrides, and the like. An electric circuit 222 for controlling electrical stimulation and for processing the data detected from nanopore cell 200 may be formed on substrate 230 and/or within dielectric layer 201. For example, a plurality of patterned metal layers (e.g., metal 1 to metal 6) may be formed in dielectric layer 201, and a plurality of active devices (e.g., transistors) may be fabricated on substrate 230. In some embodiments, signal source 228 is included as a part of electric circuit 222. Electric circuit 222 may include, for example, amplifiers, integrators, analog-to-digital converters, noise filters, feedback control logic, and/or various other components. Electric circuit 222 may be further coupled to a processor 224 that is coupled to a memory 226, where processor 224 can analyze the sequencing data to determine sequences of the polymer molecules that have been sequenced in the array.

Working electrode 202 may be formed on dielectric layer 201, and may form at least a part of the bottom of well 205. In some embodiments, working electrode 202 is a metal electrode. For non-faradaic conduction, working electrode 202 may be made of metals or other materials that are resistant to corrosion and oxidation, such as, for example, platinum, gold, titanium nitride, and graphite. For example, working electrode 202 may be a platinum electrode with electroplated platinum. In another example, working electrode 202 may be a titanium nitride (TiN) working electrode. Working electrode 202 may be porous, thereby increasing its surface area and a resulting capacitance associated with working electrode 202. Because the working electrode of a nanopore cell may be independent from the working electrode of another nanopore cell, the working electrode may be referred to as cell electrode in this disclosure.

Dielectric layer 204 may be formed above dielectric layer 201. Dielectric layer 204 forms the walls surrounding well 205. Dielectric material used to form dielectric layer 204 may include, for example, glass, oxide, silicon mononitride (SiN), polyimide, or other suitable hydrophobic insulating material. The top surface of dielectric layer 204 may be silanized. The silanization may form a hydrophobic layer 220 above the top surface of dielectric layer 204. In some embodiments, hydrophobic layer 220 has a thickness of about 1.5 nanometer (nm).

Well 205 formed by the walls of dielectric layer 204 includes volume of electrolyte 206 above working electrode 202. Volume of electrolyte 206 may be buffered and may include one or more of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride (CaCl$_2$), strontium chloride (SrCl$_2$), manganese chloride (MnCl$_2$), and magnesium chloride (MgCl$_2$). In some embodiments, volume of electrolyte 206 has a thickness of about three microns (μm).

As also shown in FIG. 2, a membrane may be formed on top of dielectric layer 204 and span across well 205. In some embodiments, the membrane may include a lipid monolayer 218 formed on top of hydrophobic layer 220. As the membrane reaches the opening of well 205, lipid monolayer 218 may transition to lipid bilayer 214 that spans across the opening of well 205. The lipid bilayer may comprise or consist of phospholipid, for example, selected from diphytanoyl-phosphatidylcholine (DPhPC), 1,2-diphytanoyl-sn-glycero-3-phosphocholine, 1,2-Di-O-Phytanyl-sn-Glycero-3-phosphocholine (DoPhPC), palmitoyl-oleoyl-phosphatidylcholine (POPC), dioleoyl-phosphatidyl-methylester (DOPME), dipalmitoylphosphatidylcholine (DPPC), phosphatidylcholine, phosphatidylethanolamine, phosphatidylserine, phosphatidic acid, phosphatidylinositol, phosphatidylglycerol, sphingomyelin, 1,2-di-O-phytanyl-sn-glycerol; 1,2-dipalmitoyl-sn-glycero-3-phosphoethanolamine-N-[methoxy(polyethylene glycol)-350]; 1,2-dipalmitoyl-sn-glycero-3-phosphoethanolamine-N-[methoxy(polyethylene glycol)-550]; 1,2-dipalmitoyl-sn-glycero-3-phosphoethanolamine-N-[methoxy(polyethylene glycol)-750]; 1,2-dipalmitoyl-sn-glycero-3-phosphoethanolamine-N-[methoxy(polyethylene glycol)-1000]; 1,2-dipalmitoyl-sn-glycero-3-phosphoethanolamine-N-[methoxy (polyethylene glycol)-2000]; 1,2-dioleoyl-sn-glycero-3-phosphoethanolamine-N-lactosyl; GM1 Ganglioside, Lysophosphatidylcholine (LPC) or any combination thereof.

As shown, lipid bilayer 214 is embedded with a single nanopore 216, e.g., formed by a single PNTMC. As described above, nanopore 216 may be formed by inserting a single PNTMC into lipid bilayer 214 by electroporation. Nanopore 216 may be large enough for passing at least a portion of the analyte of interest and/or small ions (e.g., Na$^+$, K$^+$, Ca$^{2+}$, Cl$^-$) between the two sides of lipid bilayer 214.

Sample chamber 215 is over lipid bilayer 214, and can hold a solution of the analyte of interest for characterization. The solution may be an aqueous solution containing bulk electrolyte 208 and buffered to an optimum ion concentration and maintained at an optimum pH to keep the nanopore 216 open. Nanopore 216 crosses lipid bilayer 214 and provides the only path for ionic flow from bulk electrolyte 208 to working electrode 202. In addition to nanopores (e.g., PNTMCs) and the analyte of interest, bulk electrolyte 208 may further include one or more of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride (CaCl$_2$), strontium chloride (SrCl$_2$), Manganese chloride (MnCl$_2$), and magnesium chloride (MgCl$_2$).

Counter electrode (CE) 210 may be an electrochemical potential sensor. In some embodiments, counter electrode 210 may be shared between a plurality of nanopore cells, and may therefore be referred to as a common electrode. In some cases, the common potential and the common electrode may be common to all nanopore cells, or at least all nanopore cells within a particular grouping. The common electrode can be configured to apply a common potential to the bulk electrolyte 208 in contact with the nanopore 216. Counter electrode 210 and working electrode 202 may be coupled to signal source 228 for providing electrical stimulus (e.g., voltage bias) across lipid bilayer 214, and may be used for sensing electrical characteristics of lipid bilayer 214 (e.g., resistance, capacitance, and ionic current flow). In some embodiments, nanopore cell 200 can also include a reference electrode 212.

In some embodiments, various checks can be made during creation of the nanopore cell as part of calibration. Once a nanopore cell is created, further calibration steps can be performed, e.g., to identify nanopore cells that are performing as desired (e.g., one nanopore in the cell). Such calibration checks can include physical checks, voltage calibration, open channel calibration, and identification of cells with a single nanopore.

B. Detection Signals of Nanopore Sequencing Cell

Nanopore cells in nanopore sensor chip, such as nanopore cells 150 in nanopore sensor chip 100, may enable parallel sequencing using a single molecule nanopore-based sequencing by synthesis (Nano-SBS) technique.

Figure 3:
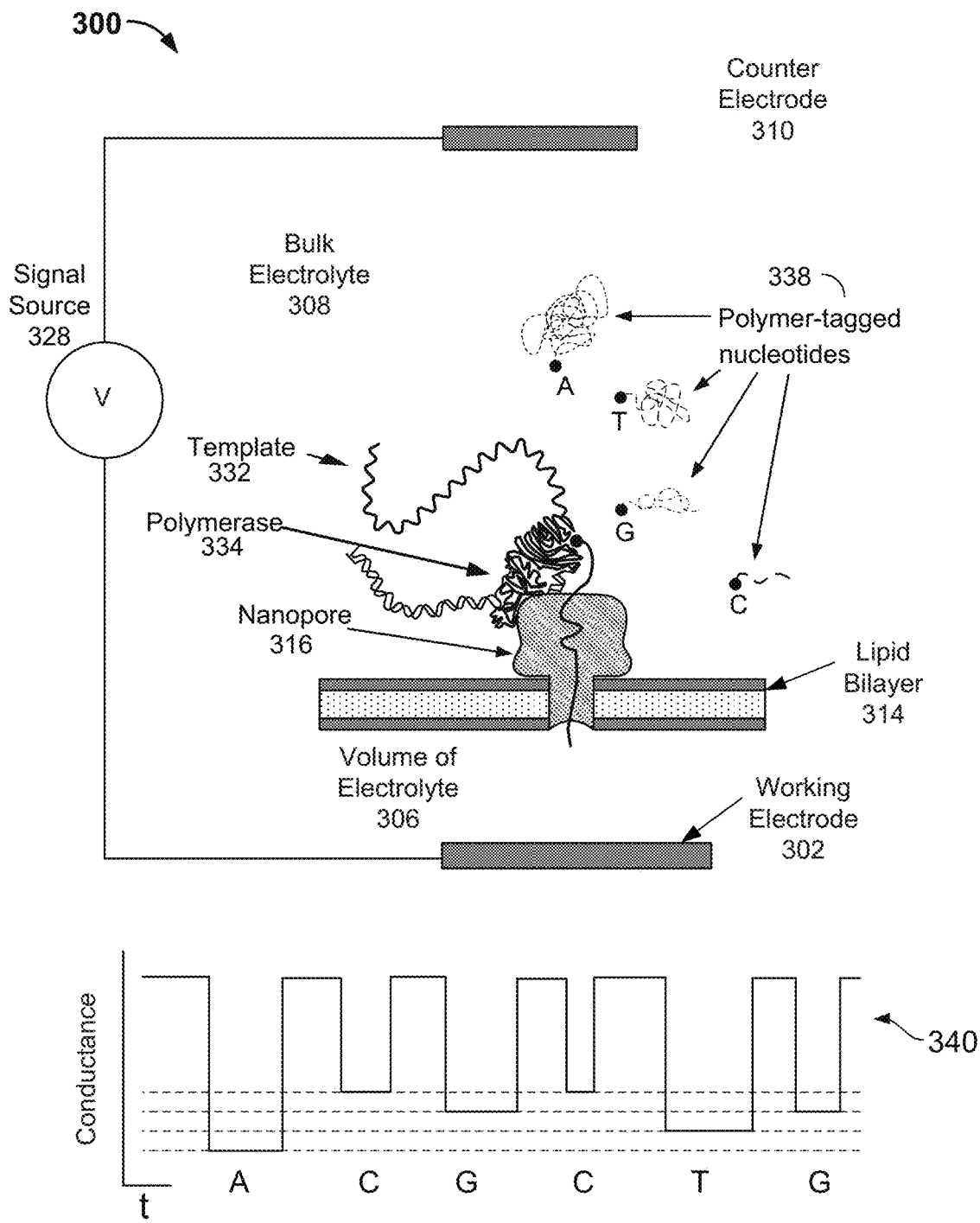
FIG. 3 illustrates an embodiment of a nanopore cell performing nucleotide sequencing using a nanopore-based sequencing-by-synthesis (Nano-SBS) technique.

FIG. 3 illustrates an embodiment of a nanopore cell 300 performing nucleotide sequencing using the Nano-SBS technique. In the Nano-SBS technique, a template 332 to be sequenced (e.g., a nucleotide acid molecule or another analyte of interest) and a primer may be introduced into bulk electrolyte 308 in the sample chamber of nanopore cell 300. As examples, template 332 can be circular or linear. A nucleic acid primer may be hybridized to a portion of template 332 to which four differently polymer-tagged nucleotides 338 may be added.

In some embodiments, an enzyme (e.g., a polymerase 334, such as a DNA polymerase) may be associated with nanopore 316 for use in the synthesizing a complementary strand to template 332. For example, polymerase 334 may be covalently attached to nanopore 316. Polymerase 334 may catalyze the incorporation of nucleotides 338 onto the primer using a single stranded nucleic acid molecule as the template. Nucleotides 338 may comprise tag species ("tags") with the nucleotide being one of four different types: A, T, G, or C. When a tagged nucleotide is correctly complexed with polymerase 334, the tag may be pulled (loaded) into the nanopore by an electrical force, such as a force generated in the presence of an electric field generated by a voltage applied across lipid bilayer 314 and/or nanopore 316. The tail of the tag may be positioned in the barrel of nanopore 316. The tag held in the barrel of nanopore 316 may generate a unique ionic blockade signal 340 due to the tag's distinct chemical structure and/or size, thereby electronically identifying the added base to which the tag attaches.

As used herein, a "loaded" or "threaded" tag may be one that is positioned in and/or remains in or near the nanopore for an appreciable amount of time, e.g., 0.1 millisecond (ms) to 10000 ms. In some cases, a tag is loaded in the nanopore prior to being released from the nucleotide. In some instances, the probability of a loaded tag passing through (and/or being detected by) the nanopore after being released upon a nucleotide incorporation event is suitably high, e.g., 90% to 99%.

In some embodiments, before polymerase 334 is connected to nanopore 316, the conductance of nanopore 316 may be high, such as, for example, about 300 picosiemens (300 pS). As the tag is loaded in the nanopore, a unique conductance signal (e.g., signal 340) is generated due to the tag's distinct chemical structure and/or size. For example, the conductance of the nanopore can be about 60 pS, 80 pS, 100 pS, or 120 pS, each corresponding to one of the four types of tagged nucleotides. The polymerase may then undergo an isomerization and a transphosphorylation reaction to incorporate the nucleotide into the growing nucleic acid molecule and release the tag molecule.

In some cases, some of the tagged nucleotides may not match (complementary bases) with a current position of the nucleic acid molecule (template). The tagged nucleotides that are not base-paired with the nucleic acid molecule may also pass through the nanopore. These non-paired nucleotides can be rejected by the polymerase within a time scale that is shorter than the time scale for which correctly paired nucleotides remain associated with the polymerase. Tags bound to non-paired nucleotides may pass through the nanopore quickly, and be detected for a short period of time (e.g., less than 10 ms), while tags bounded to paired nucleotides can be loaded into the nanopore and detected for a long period of time (e.g., at least 10 ms). Therefore, non-paired nucleotides may be identified by a downstream processor based at least in part on the time for which the nucleotide is detected in the nanopore.

A conductance (or equivalently the resistance) of the nanopore including the loaded (threaded) tag can be measured via a current passing through the nanopore, thereby providing an identification of the tag species and thus the nucleotide at the current position. In some embodiments, a direct current (DC) signal can be applied to the nanopore cell (e.g., so that the direction at which the tag moves through the nanopore is not reversed). However, operating a nanopore sensor for long periods of time using a direct current can change the composition of the electrode, unbalance the ion concentrations across the nanopore, and have other undesirable effects that can affect the lifetime of the nanopore cell. Applying an alternating current (AC) waveform can reduce the electro-migration to avoid these undesirable effects and have certain advantages as described below. The nucleic acid sequencing methods described herein that utilize tagged nucleotides are fully compatible with applied AC voltages, and therefore an AC waveform can be used to achieve these advantages.

The ability to re-charge the electrode during the AC detection cycle can be advantageous when sacrificial electrodes, electrodes that change molecular character in the current-carrying reactions (e.g., electrodes comprising silver), or electrodes that change molecular character in current-carrying reactions are used. An electrode may deplete during a detection cycle when a direct current signal is used. The recharging can prevent the electrode from reaching a depletion limit, such as becoming fully depleted, which can be a problem when the electrodes are small (e.g., when the electrodes are small enough to provide an array of electrodes having at least 500 electrodes per square millimeter). Electrode lifetime in some cases scales with, and is at least partly dependent on, the width of the electrode.

Suitable conditions for measuring ionic currents passing through the nanopores are known in the art and examples are provided herein. The measurement may be carried out with a voltage applied across the membrane and pore. In some embodiments, the voltage used may range from −400 mV to +400 mV. The voltage used is preferably in a range having a lower limit selected from −400 mV, −300 mV, −200 mV, −150 mV, −100 mV, −50 mV, −20 mV, and 0 mV, and an upper limit independently selected from +10 mV, +20 mV, +50 mV, +100 mV, +150 mV, +200 mV, +300 mV, and +400 mV. The voltage used may be more preferably in the range of 100 mV to 240 mV and most preferably in the range of 160 mV to 240 mV. It is possible to increase discrimination between different nucleotides by a nanopore using an increased applied potential. Sequencing nucleic acids using AC waveforms and tagged nucleotides is described in US Patent Publication No. US 2014/0134616 entitled "Nucleic Acid Sequencing Using Tags," filed on Nov. 6, 2013, which is herein incorporated by reference in its entirety. In addition to the tagged nucleotides described in US 2014/0134616, sequencing can be performed using nucleotide analogs that lack a sugar or acyclic moiety, e.g., (S)-Glycerol nucleoside triphosphates (gNTPs) of the five common nucleobases: adenine, cytosine, guanine, uracil, and thymine (Horhota et al., Organic Letters, 8:5345-5347 [2006]).

C. Electric Circuit of Nanopore Sequencing Cell

Figure 4:
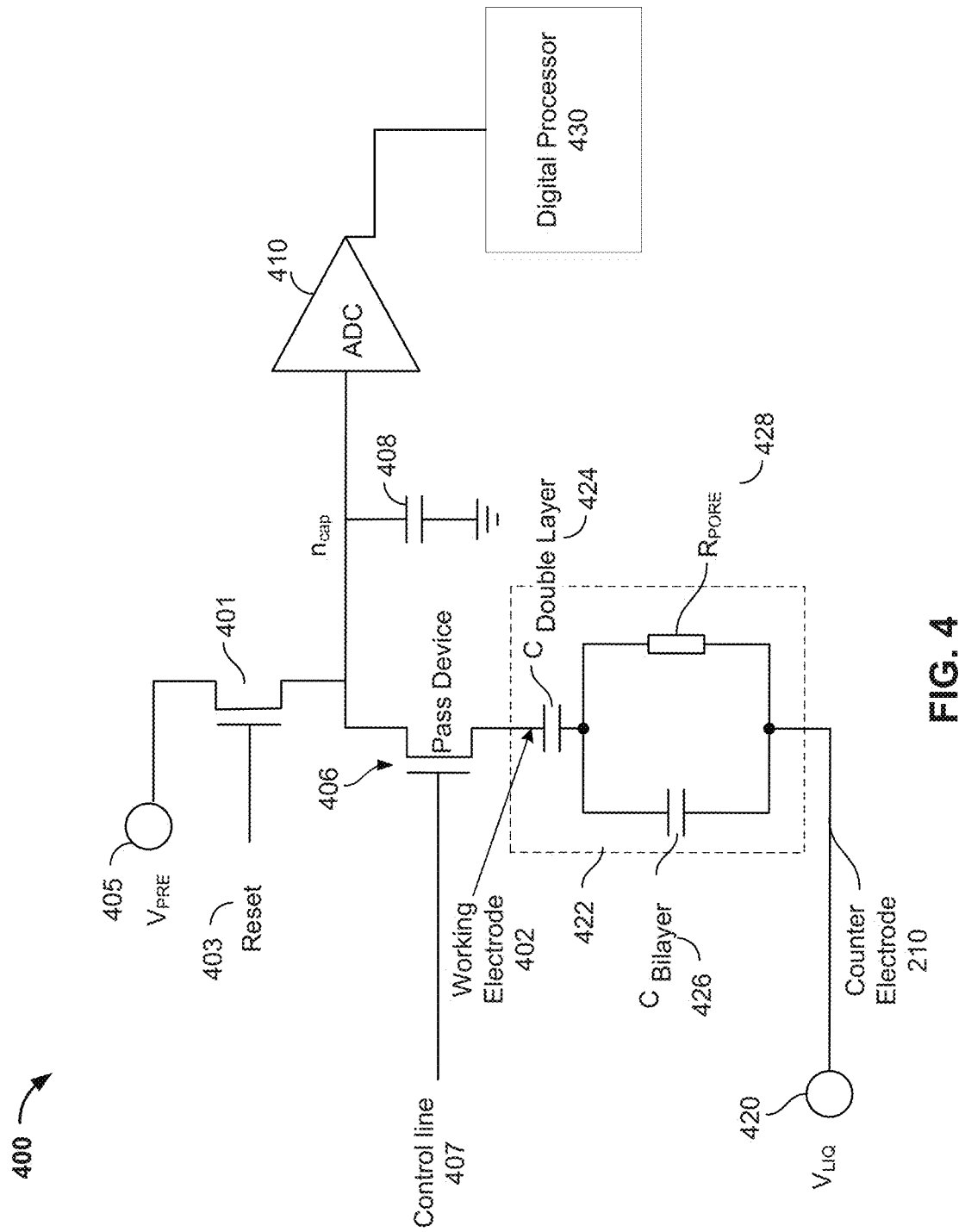
FIG. 4 illustrates an embodiment of an electric circuit in a nanopore cell.

FIG. 4 illustrates an embodiment of an electric circuit 400 (which may include portions of electric circuit 222 in FIG. 2) in a nanopore cell, such as nanopore cell 200. As described above, in some embodiments, electric circuit 400 includes a counter electrode 210 that may be shared between a plurality of nanopore cells or all nanopore cells in a nanopore sensor chip, and may therefore also be referred to as a common electrode. The common electrode can be configured to apply a common potential to the bulk electrolyte (e.g., bulk electrolyte 208) in contact with the lipid bilayer (e.g., lipid bilayer 214) in the nanopore cells by connecting to a alternating voltage source 420 ($V_{LIQ}$). In some embodiments, an AC non-Faradaic mode may be utilized to modulate voltage $V_{LIQ}$ with an AC signal (e.g., a square wave) and apply it to the bulk electrolyte in contact with the lipid bilayer in the nanopore cell. In some embodiments, $V_{LIQ}$ is a square wave with a magnitude of ±200-250 mV and a frequency between, for example, 25 and 400 Hz. The bulk electrolyte between counter electrode 210 and the lipid bilayer (e.g., lipid bilayer 214) may be modeled by a large capacitor (not shown), such as, for example, 100 g or larger.

FIG. 4 also shows an electrical model 422 representing the electrical properties of a working electrode (e.g., working electrode 202) and the lipid bilayer (e.g., lipid bilayer 214). Electrical model 422 includes a capacitor 426 ($C_{Bilayer}$) that models a capacitance associated with the lipid bilayer and a resistor 428 ($R_{PORE}$) that models a variable resistance associated with the nanopore, which can change based on the presence of a particular tag in the nanopore. Electrical model 422 also includes a capacitor 424 having a double layer capacitance ($C_{Double\ Layer}$) and representing the electrical properties of working electrode 202 and well 205. Working electrode 202 may be configured to apply a distinct potential independent from the working electrodes in other nanopore cells.

Pass device 406 is a switch that can be used to connect or disconnect the lipid bilayer and the working electrode from electric circuit 400. Pass device 406 may be controlled by control line 407 to enable or disable a voltage stimulus to be applied across the lipid bilayer in the nanopore cell. Before lipids are deposited to form the lipid bilayer, the impedance between the two electrodes may be very low because the well of the nanopore cell is not sealed, and therefore pass device 406 may be kept open to avoid a short-circuit condition. Pass device 406 may be closed after lipid solvent has been deposited to the nanopore cell to seal the well of the nanopore cell.

Electric circuit 400 may further include an on-chip integrating capacitor 408 ($n_{cap}$). Integrating capacitor 408 may be pre-charged by using a reset signal 403 to close switch 401, such that integrating capacitor 408 is connected to a voltage source $V_{PRE}$ 405. In some embodiments, voltage source $V_{PRE}$ 405 provides a constant reference voltage with a magnitude of, for example, 900 mV. When switch 401 is closed, integrating capacitor 408 may be pre-charged to the reference voltage level of voltage source $V_{PRE}$ 405.

After integrating capacitor 408 is pre-charged, reset signal 403 may be used to open switch 401 such that integrating capacitor 408 is disconnected from voltage source $V_{PRE}$ 405. At this point, depending on the level of voltage source $V_{LIQ}$, the potential of counter electrode 210 may be at a level higher than the potential of working electrode 202 (and integrating capacitor 408), or vice versa. For example, during a positive phase of a square wave from voltage source $V_{LIQ}$ (e.g., the bright or dark period of the AC voltage source signal cycle), the potential of counter electrode 210 is at a level higher than the potential of working electrode 202. During a negative phase of the square wave from voltage source $V_{LIQ}$ (e.g., the dark or bright period of the AC voltage source signal cycle), the potential of counter electrode 210 is at a level lower than the potential of working electrode 202. Thus, in some embodiments, integrating capacitor 408 may be further charged during the bright period from the pre-charged voltage level of voltage source $V_{PRE}$ 405 to a higher level, and discharged during the dark period to a lower level, due to the potential difference between counter electrode 210 and working electrode 202. In other embodiments, the charging and discharging may occur in dark periods and bright periods, respectively.

Integrating capacitor 408 may be charged or discharged for a fixed period of time, depending on the sampling rate of an analog-to-digital converter (ADC) 410, which may be higher than 1 kHz, 5 kHz, 10 kHz, 100 kHz, or more. For example, with a sampling rate of 1 kHz, integrating capacitor 408 may be charged/discharged for a period of about 1 ms, and then the voltage level may be sampled and converted by ADC 410 at the end of the integration period. A particular voltage level would correspond to a particular tag species in the nanopore, and thus correspond to the nucleotide at a current position on the template.

After being sampled by ADC 410, integrating capacitor 408 may be pre-charged again by using reset signal 403 to close switch 401, such that integrating capacitor 408 is connected to voltage source $V_{PRE}$ 405 again. The steps of pre-charging integrating capacitor 408, waiting for a fixed period of time for integrating capacitor 408 to charge or discharge, and sampling and converting the voltage level of integrating capacitor by ADC 410 can be repeated in cycles throughout the sequencing process.

A digital processor 430 can process the ADC output data, e.g., for normalization, data buffering, data filtering, data compression, data reduction, event extraction, or assembling ADC output data from the array of nanopore cells into various data frames. In some embodiments, digital processor 430 can perform further downstream processing, such as base determination. Digital processor 430 can be implemented as hardware (e.g., in a GPU, FPGA, ASIC, etc.) or as a combination of hardware and software.

Accordingly, the voltage signal applied across the nanopore can be used to detect particular states of the nanopore. One of the possible states of the nanopore is an open-channel state when a tag-attached polyphosphate is absent from the barrel of the nanopore, also referred to herein as the unthreaded state of the nanopore. Another four possible states of the nanopore each correspond to a state when one of the four different types of tag-attached polyphosphate nucleotides (A, T, G, or C) is held in the barrel of the nanopore. Yet another possible state of the nanopore is when the lipid bilayer is ruptured.

When the voltage level on integrating capacitor 408 is measured after a fixed period of time, the different states of a nanopore may result in measurements of different voltage levels. This is because the rate of the voltage decay (decrease by discharging or increase by charging) on integrating capacitor 408 (i.e., the steepness of the slope of a voltage on integrating capacitor 408 versus time plot) depends on the nanopore resistance (e.g., the resistance of resistor $R_{PORE}$ 428). More particularly, as the resistance associated with the nanopore in different states is different due to the molecules' (tags') distinct chemical structures, different corresponding rates of voltage decay may be observed and may be used to identify the different states of the nanopore. The voltage decay curve may be an exponential curve with an RC time constant $\tau = RC$, where R is the resistance associated with the nanopore (i.e., $R_{PORE}$ 428) and C is the capacitance associated with the membrane (i.e., capacitor 426 ($C_{Bilayer}$)) in parallel with R. A time constant of the nanopore cell can be, for example, about 200-500 ms. The decay curve may not fit exactly to an exponential curve due to the detailed implementation of the bilayer, but the decay curve may be similar to an exponential curve and is monotonic, thus allowing detection of tags.

In some embodiments, the resistance associated with the nanopore in an open-channel state may be in the range of 100 MOhm to 20 GOhm. In some embodiments, the resistance associated with the nanopore in a state where a tag is inside the barrel of the nanopore may be within the range of 200 MOhm to 40 GOhm. In other embodiments, integrating capacitor 408 may be omitted, as the voltage leading to ADC 410 will still vary due to the voltage decay in electrical model 422.

The rate of the decay of the voltage on integrating capacitor 408 may be determined in different ways. As explained above, the rate of the voltage decay may be determined by measuring a voltage decay during a fixed time interval. For example, the voltage on integrating capacitor 408 may be first measured by ADC 410 at time t1, and then the voltage is measured again by ADC 410 at time t2. The voltage difference is greater when the slope of the voltage on integrating capacitor 408 versus time curve is steeper, and the voltage difference is smaller when the slope of the voltage curve is less steep. Thus, the voltage difference may be used as a metric for determining the rate of the decay of the voltage on integrating capacitor 408, and thus the state of the nanopore cell.

In other embodiments, the rate of the voltage decay can be determined by measuring a time duration that is required for a selected amount of voltage decay. For example, the time required for the voltage to drop or increase from a first voltage level V1 to a second voltage level V2 may be measured. The time required is less when the slope of the voltage vs. time curve is steeper, and the time required is greater when the slope of the voltage vs. time curve is less steep. Thus, the measured time required may be used as a metric for determining the rate of the decay of the voltage on integrating capacitor $n_{cap}$ 408, and thus the state of the nanopore cell. One skilled in the art will appreciate the various circuits that can be used to measure the resistance of the nanopore, e.g., including current measurement techniques.

In some embodiments, electric circuit 400 may not include a pass device (e.g., pass device 406) and an extra capacitor (e.g., integrating capacitor 408 ($n_{cap}$)) that are fabricated on-chip, thereby facilitating the reduction in size of the nanopore-based sequencing chip. Due to the thin nature of the membrane (lipid bilayer), the capacitance associated with the membrane (e.g., capacitor 426 ($C_{Bilayer}$)) alone can suffice to create the required RC time constant without the need for additional on-chip capacitance. Therefore, capacitor 426 may be used as the integrating capacitor, and may be pre-charged by the voltage signal $V_{PRE}$ and subsequently be discharged or charged by the voltage signal $V_{LIQ}$. The elimination of the extra capacitor and the pass device that are otherwise fabricated on-chip in the electric circuit can significantly reduce the footprint of a single nanopore cell in the nanopore sequencing chip, thereby facilitating the scaling of the nanopore sequencing chip to include more and more cells (e.g., having millions of cells in a nanopore sequencing chip).

D. Data Sampling in Nanopore Cell

To perform sequencing of a nucleic acid, the voltage level of integrating capacitor (e.g., integrating capacitor 408 ($n_{cap}$) or capacitor 426 ($C_{Bilayer}$)) can be sampled and converted by the ADC (e.g., ADC 410) while a tagged nucleotide is being added to the nucleic acid. The tag of the nucleotide can be pushed into the barrel of the nanopore by the electric field across the nanopore that is applied through the counter electrode and the working electrode, for example, when the applied voltage is such that $V_{LIQ}$ is lower than $V_{PRE}$.

1. Threading

A threading event is when a tagged nucleotide is attached to the template (e.g., nucleic acid fragment), and the tag goes in and out of the barrel of the nanopore. This can happen multiple times during a threading event. When the tag is in the barrel of the nanopore, the resistance of the nanopore may be higher, and a lower current may flow through the nanopore.

During sequencing, a tag may not be in the nanopore in some AC cycles (referred to as an open-channel state), where the current is the highest because of the lower resistance of the nanopore. When a tag is attracted into the barrel of the nanopore, the nanopore is in a bright mode. When the tag is pushed out of the barrel of the nanopore, the nanopore is in a dark mode.

2. Bright and Dark Period

During an AC cycle, the voltage on integrating capacitor may be sampled multiple times by the ADC. For example, in one embodiment, an AC voltage signal is applied across the system at, e.g., about 100 Hz, and an acquisition rate of the ADC can be about 2000 Hz per cell. Thus, there can be about 20 data points (voltage measurements) captured per AC cycle (cycle of an AC waveform). Data points corresponding to one cycle of the AC waveform may be referred to as a set. In a set of data points for an AC cycle, there may be a subset captured when, for example, $V_{LIQ}$ is lower than $V_{PRE}$, which may correspond to a bright mode (period) where the tag is forced into the barrel of the nanopore. Another subset may correspond to a dark mode (period) where the tag is pushed out of the barrel of the nanopore by the applied electric field when, for example, $V_{LIQ}$ is higher than $V_{PRE}$.

3. Measured Voltages

For each data point, when the switch 401 is opened, the voltage at the integrating capacitor (e.g., integrating capacitor 408 ($n_{cap}$) or capacitor 426 ($C_{Bilayer}$)) will change in a decaying manner as a result of the charging/discharging by $V_{LIQ}$, e.g., as an increase from $V_{PRE}$ to $V_{LIQ}$ when $V_{LIQ}$ is higher than $V_{PRE}$ or a decrease from $V_{PRE}$ to $V_{LIQ}$ when $V_{LIQ}$ is lower than $V_{PRE}$. The final voltage values may deviate from $V_{LIQ}$ as the working electrode charges. The rate of change of the voltage level on the integrating capacitor may be governed by the value of the resistance of the bilayer, which may include the nanopore, which may in turn include a molecule (e.g., a tag of a tagged nucleotides) in the nanopore. The voltage level can be measured at a predetermined time after switch 401 opens.

Switch 401 may operate at the rate of data acquisition. Switch 401 may be closed for a relatively short time period between two acquisitions of data, typically right after a measurement by the ADC. The switch allows multiple data points to be collected during each sub-period (bright or dark) of each AC cycle of $V_{LIQ}$. If switch 401 remains open, the voltage level on the integrating capacitor, and thus the output value of the ADC, would fully decay and stay there. Instead, when switch 401 is closed, the integrating capacitor is precharged again (to $V_{PRE}$) and becomes ready for another measurement. Thus, switch 401 allows multiple data points to be collected for each sub-period (bright or dark) of each AC cycle. Such multiple measurements can allow higher resolution with a fixed ADC (e.g. 8-bit to 14-bit due to the greater number of measurements, which may be averaged). The multiple measurements can also provide kinetic information about the molecule threaded into the nanopore. The timing information may allow the determination of how long a threading takes place. This can also be used in helping to determine whether multiple nucleotides that are added to the nucleic acid strand are being sequenced.

Figure 5:
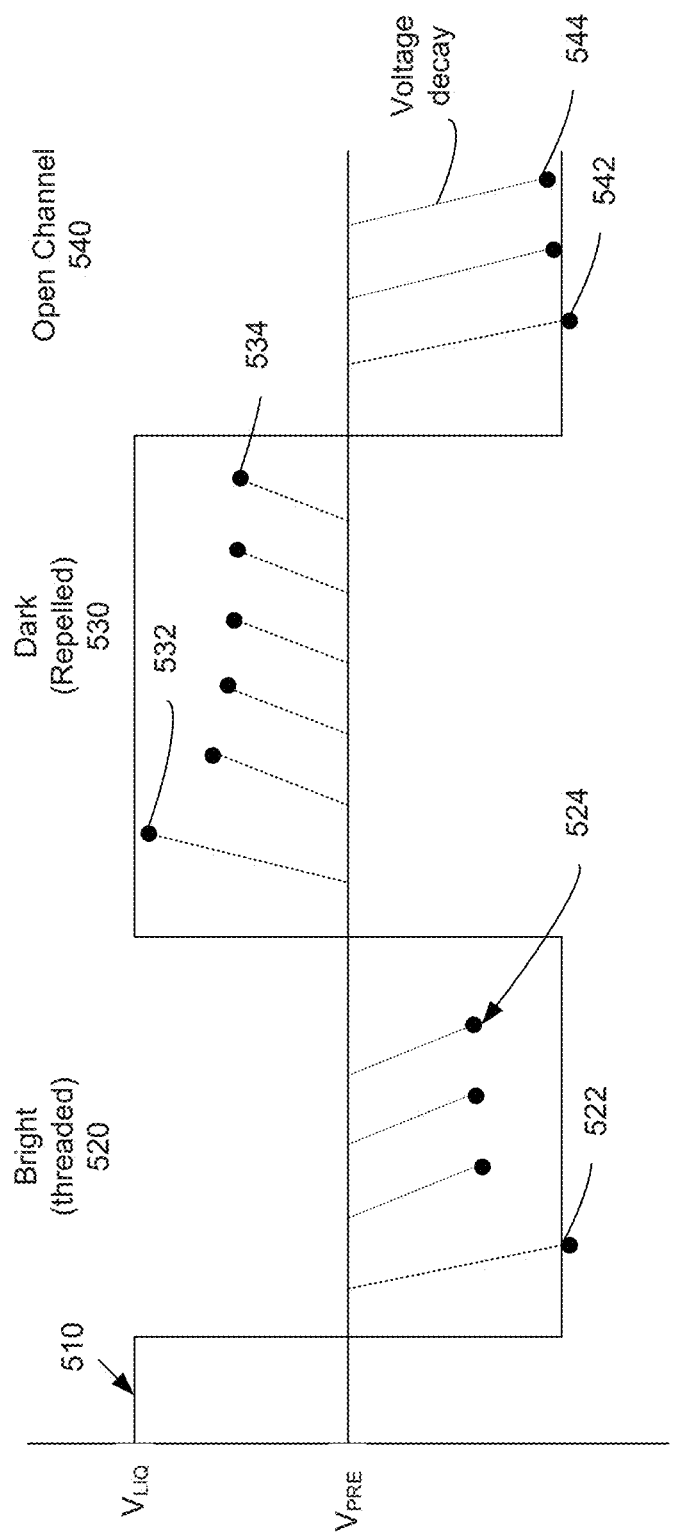
FIG. 5 shows example data points captured from a nanopore cell during bright periods and dark periods of AC cycles, according to certain aspects of the present disclosure.

FIG. 5 shows example data points captured from a nanopore cell during bright periods and dark periods of AC cycles. In FIG. 5, the change in the data points is exaggerated for illustration purpose. The voltage ($V_{PRE}$) applied to the working electrode or the integrating capacitor is at a constant level, such as, for example, 900 mV. A voltage signal 510 ($V_{LIQ}$) applied to the counter electrode of the nanopore cells is an AC signal shown as a rectangular wave, where the duty cycle may be any suitable value, such as less than or equal to 50%, for example, about 40%.

During a bright period 520, voltage signal 510 ($V_{LIQ}$) applied to the counter electrode is lower than the voltage $V_{PRE}$ applied to the working electrode, such that a tag may be forced into the barrel of the nanopore by the electric field caused by the different voltage levels applied at the working electrode and the counter electrode (e.g., due to the charge on the tag and/or flow of the ions). When switch 401 is opened, the voltage at a node before the ADC (e.g., at an integrating capacitor) will decrease. After a voltage data point is captured (e.g., after a specified time period), switch 401 may be closed and the voltage at the measurement node will increase back to $V_{PRE}$ again. The process can repeat to measure multiple voltage data points. In this way, multiple data points may be captured during the bright period.

As shown in FIG. 5, a first data point 522 (also referred to as first point delta (FPD)) in the bright period after a change in the sign of the $V_{LIQ}$ signal may be lower than subsequent data points 524. This may be because there is no tag in the nanopore (open channel), and thus it has a low resistance and a high discharge rate. In some instances, first data point 522 may exceed the $V_{LIQ}$ level as shown in FIG. 5. This may be caused by the capacitance of the bilayer coupling the signal to the on-chip capacitor. Data points 524 may be captured after a threading event has occurred, i.e., a tag is forced into the barrel of the nanopore, where the resistance of the nanopore and thus the rate of discharging of the integrating capacitor depends on the particular type of tag that is forced into the barrel of the nanopore. Data points 524 may decrease slightly for each measurement due to charge built up at $C_{Double\ Layer}$ 424, as mentioned below.

During a dark period 530, voltage signal 510 ($V_{LIQ}$) applied to the counter electrode is higher than the voltage ($V_{PRE}$) applied to the working electrode, such that any tag would be pushed out of the barrel of the nanopore. When switch 401 is opened, the voltage at the measurement node increases because the voltage level of voltage signal 510 ($V_{LIQ}$) is higher than $V_{PRE}$. After a voltage data point is captured (e.g., after a specified time period), switch 401 may be closed and the voltage at the measurement node will decrease back to $V_{PRE}$ again. The process can repeat to measure multiple voltage data points. Thus, multiple data points may be captured during the dark period, including a first point delta 532 and subsequent data points 534. As described above, during the dark period, any nucleotide tag is pushed out of the nanopore, and thus minimal information about any nucleotide tag is obtained, besides for use in normalization.

FIG. 5 also shows that during bright period 540, even though voltage signal 510 ($V_{LIQ}$) applied to the counter electrode is lower than the voltage ($V_{PRE}$) applied to the working electrode, no threading event occurs (open-channel). Thus, the resistance of the nanopore is low, and the rate of discharging of the integrating capacitor is high. As a result, the captured data points, including a first data point 542 and subsequent data points 544, show low voltage levels.

The voltage measured during a bright or dark period might be expected to be about the same for each measurement of a constant resistance of the nanopore (e.g., made during a bright mode of a given AC cycle while one tag is in the nanopore), but this may not be the case when charge builds up at double layer capacitor 424 ($C_{Double\ Layer}$). This charge build-up can cause the time constant of the nanopore cell to become longer. As a result, the voltage level may be shifted, thereby causing the measured value to decrease for each data point in a cycle. Thus, within a cycle, the data points may change somewhat from data point to another data point, as shown in FIG. 5.

4. Determining Bases

For each usable nanopore cell of the nanopore sensor chip, a production mode can be run to sequence nucleic acids. The ADC output data captured during the sequencing can be normalized to provide greater accuracy. Normalization can account for offset effects, such as cycle shape and baseline shift. After normalization, embodiments can determine clusters of voltages for the threaded channels, where each cluster corresponds to a different tag species, and thus a different nucleotide. The clusters can be used to determine probabilities of a given voltage corresponding to a given nucleotide. As another example, the clusters can be used to determine cutoff voltages for discriminating between different nucleotides (bases).

Further details regarding the sequencing operation can be found in, for example, U.S. Patent Publication No. 2016/0178577 entitled "Nanopore-Based Sequencing With Varying Voltage Stimulus," U.S. Patent Publication No. 2016/0178554 entitled "Nanopore-Based Sequencing With Varying Voltage Stimulus," U.S. patent application Ser. No. 15/085,700 entitled "Non-Destructive Bilayer Monitoring Using Measurement Of Bilayer Response To Electrical Stimulus," and U.S. patent application Ser. No. 15/085,713 entitled "Electrical Enhancement Of Bilayer Formation," the disclosures of which are incorporated by reference in their entirety for all purposes.

5. Periodicity of Voltage Values

Figure 6:
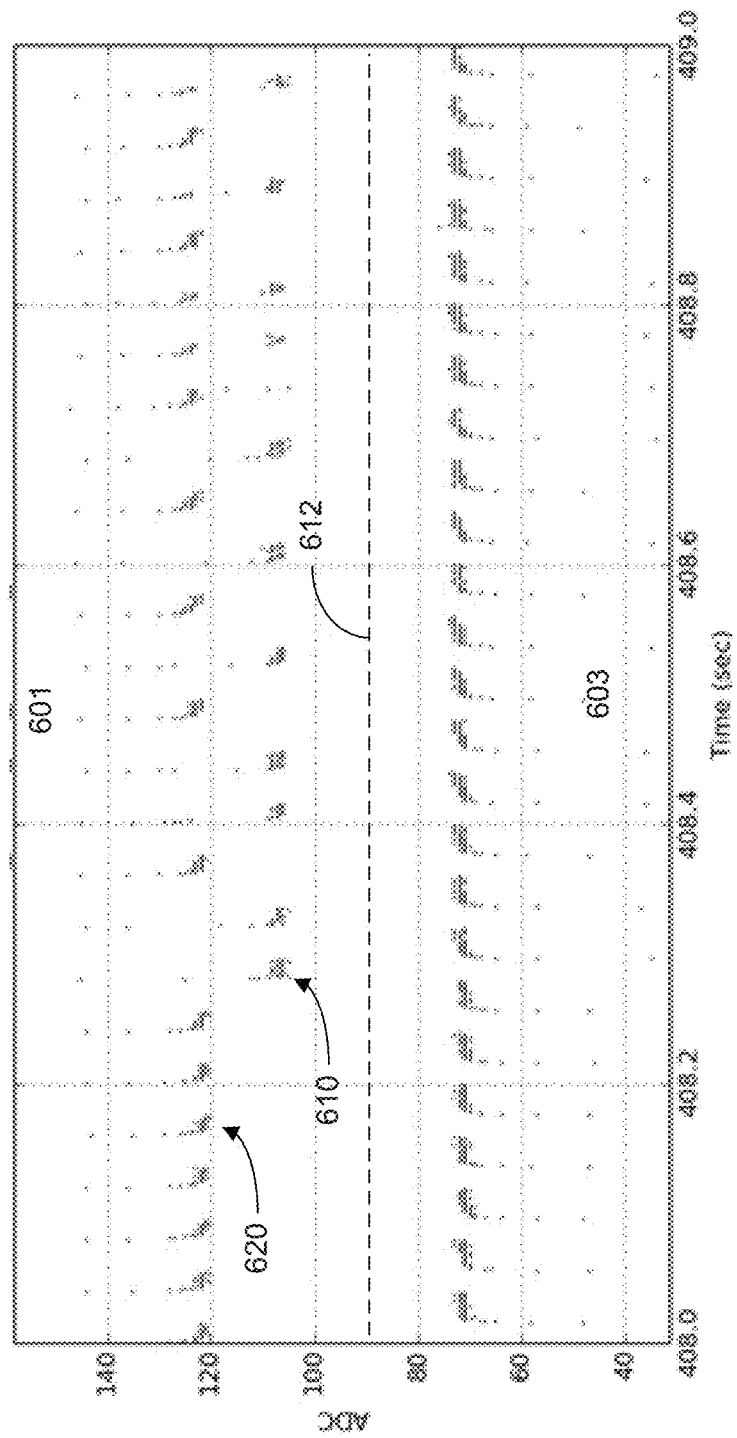
FIG. 6 shows sample data that illustrates the periodicity of voltage data, according to certain aspects of the present disclosure.

FIG. 6 shows sample bright and dark period data for a test sequencing run according to some embodiments. Bright period data are shown on top portion 601 of the figure and the dark period data are shown on the bottom portion 603 of the figure. The periodicity of the voltage data is caused by an alternating signal provided by an alternating (AC) voltage source, e.g., AC voltage source 420, as described above in reference to FIG. 4. Each data point shown in FIG. 6 is obtained by an ADC measurement of the voltage on a node of the nanopore cell circuit, e.g., at $n_{cap}$ in FIG. 4, after a certain period of time relative to the opening of pass device 406. For each measurement, the voltage at $n_{cap}$ starts at $V_{PRE}$ ($V_{PRE}$ is shown as dashed line 612) and then decays, approaching +/−$V_{LIQ}$ depending on the period (bright or dark) within the AC cycle. After a certain time delay, the ADC measures a voltage value. FIG. 6 shows the collection of these measured voltage values, i.e., each data point is a single point sample of the RC decay curve from $V_{PRE}$ to $V_{LIQ}$. For the example shown in FIG. 6, the data acquisition rate is about 1,976 Hz. Within each period, the variation in voltage from point-to-point is caused, in part, by charge buildup in the cell, leading to an overall shift in the underlying voltage decay curve for the charging/discharging of the integrating capacitor (e.g., capacitor 408 or capacitor 426, depending on the circuit used).

FIG. 6 shows data from an open channel state of the bright mode, e.g., bright mode data 620 that precedes a threading event 610 that appears shortly after the start of the bright period of the $7^{th}$ AC cycle. Subsequent open channel values and threading events in other AC cycles are also shown as time progresses. In some embodiments, as shown here, the measured ADC values in the bright periods are actually fairly repeatable from cycle to cycle for both threaded and open channel states. This opens up the possibility that the systematic offsets and noise in one bright period's data may be compensated using an adjacent (or even a subsequent non-adjacent) bright period's data, without the need to use dark channel data. The following section details one or more embodiments that make use of the periodicity of the voltage data.

III. Period-to-Period Analysis

Embodiments take advantage of the periodicity in the data, e.g., as shown in FIG. 6 above. Embodiments can use few assumptions or parameters and thus be more robust. In this manner, embodiments can be used with new systems that have a new nanopore, lipid bilayer, etc., where minimal characterization of the new cell has been done. Thus, embodiments can be broadly applicable without having much prior knowledge of the sequencing cell being used.

A. Determining a Difference Signal

To determine a difference signal, one cycle of data can be subtracted from another cycle of data. In some embodiments, corresponding data points originate from a neighboring cycle (e.g., nearest neighbor, second neighbor, etc.).

Figure 7:
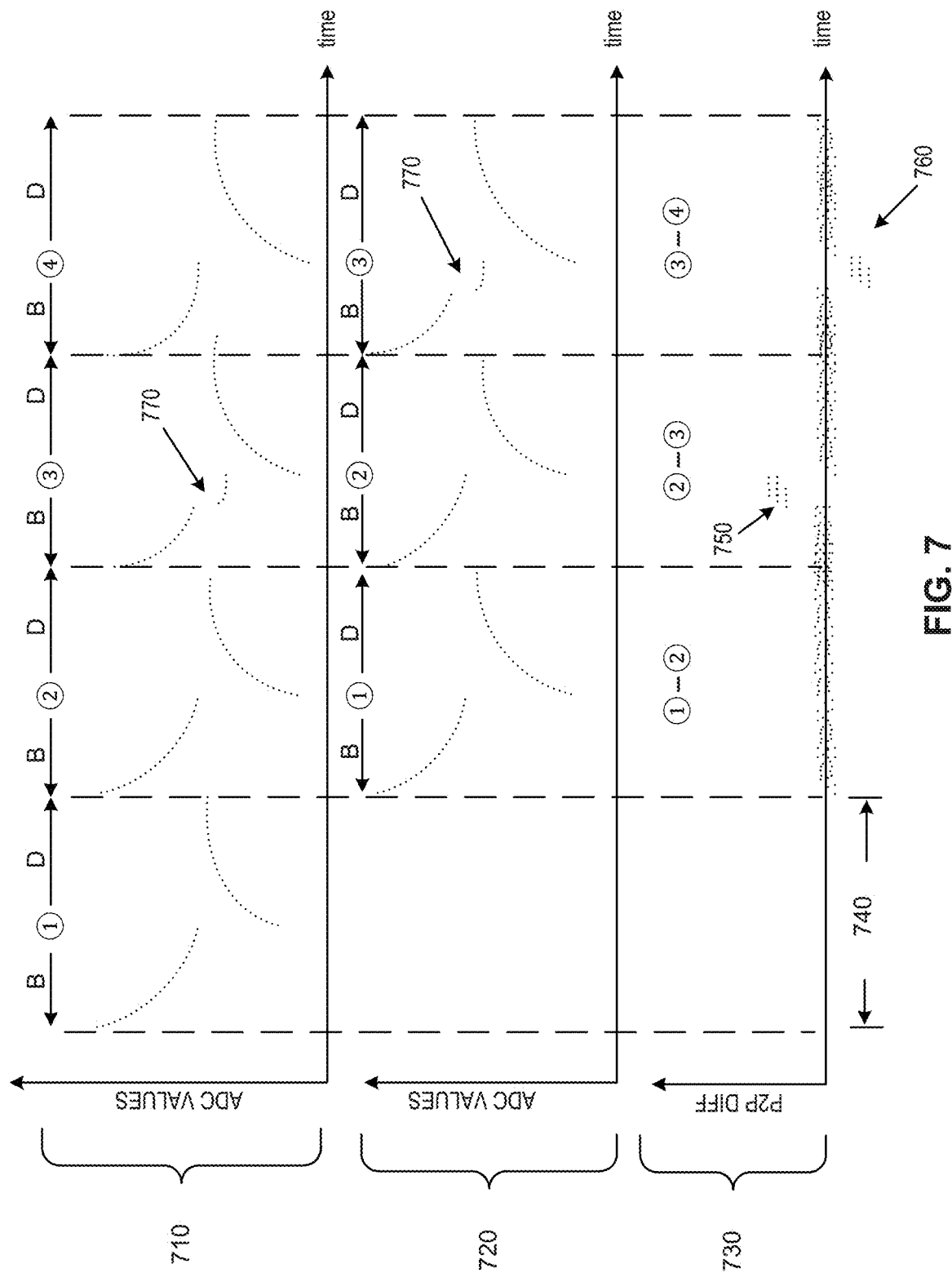
FIG. 7 illustrates shifting of voltage data for determining difference data, where the voltage data has one threading event, according to certain aspects of the present disclosure.

FIG. 7 shows sets of data points of multiple cycles 1-4 with each cycle having a respective bright and dark period, denoted by B and D labels. The determination of difference data according to some proceeds as follows. Raw ADC data (not shown) is used to create two shifted data sets, which each may be stored in memory. Signal 710 is the raw data shifted by one-half period to the left (referred to herein as left_adc) and data 720 is the raw data shifted one-half period to the right (referred to herein as right_adc). While this embodiment shows an example of a net one-period shift, other shifts are possible without departing from the scope of the present disclosure, e.g., two-period shifts, three-period shifts, etc. Further, the raw data can be used, along with shifted data that is shifted one full period, as opposed to shifting twice at a half-period. The processed difference data 730 (referred to herein as p2p_diff) can then be created by subtracting the two shifted adc-signals, in this case:

p2p_diff=left_adc−right_adc.

In some embodiments, the first cycle of processed difference data 730 (p2p_diff) is obtained by subtracting raw cycle 2 from raw cycle 1. The second cycle of processed difference data 730 (p2p_diff) is obtained by subtracting raw cycle 3 from raw cycle 2. The third cycle of processed difference data 730 (p2p_diff) is obtained by subtracting raw cycle 3 from raw cycle 4 and so on. In the processed difference data 730, the single threading event 770 from the raw data is duplicated, first appearing as a positive peak (event peak 750) and subsequently appearing again as a negative peak (event peak 760).

One of ordinary skill will appreciate that event peaks 750 and 760 are generally of opposite sign and thus, the positive and negative qualifiers are used herein as merely one example. The positive and negative peaks for this single threading event are separated in time by an amount that equals the net time shift between the two shifted data sets (one full period in this example). However, the net time shift may be longer for threading events that persist for multiple cycles.

While FIG. 7 shows a point-wise period-to-period differencing method to compute the processed difference data 730, any differencing scheme may be used without departing from the scope of the present disclosure, e.g., shifts may be in either direction (right-to-left or left-to-right) by a single or multiple of a period. FIG. 7 shows a nearest-neighbor difference by (net) shifting left-to-right by a single period. However, differences can be taken by shifting by a multiple of periods which can be provide more coarse scale information about the underlying signal.

A difference for the first cycle and/or last cycle may not be determined because there may be no first cycle data or last cycle data for one of the shifted cycles. Accordingly, these regions are referred to herein as "invalid regions." An example of a first invalid region 740 is shown in FIG. 7.

Figure 8:
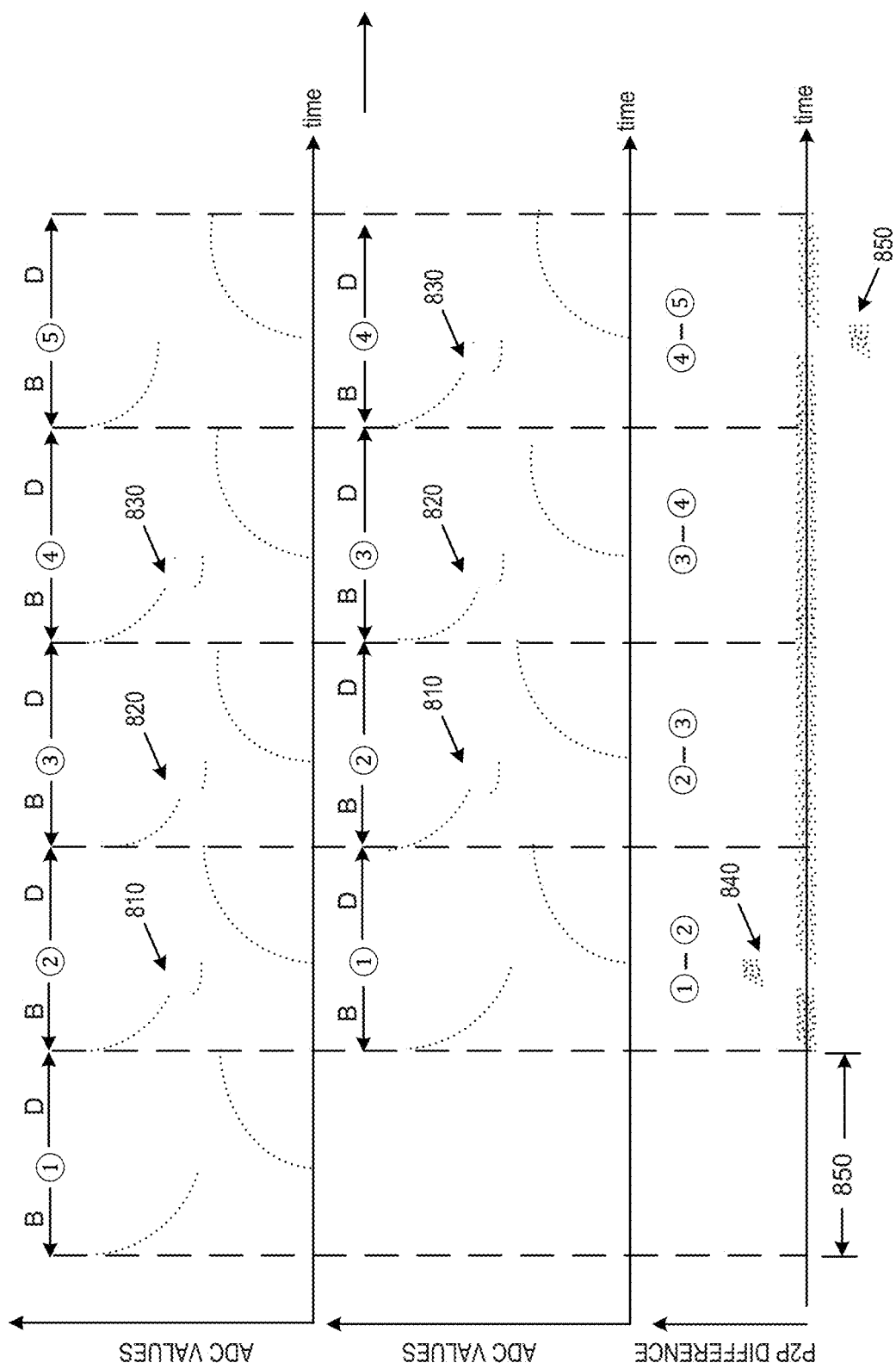
FIG. 8 illustrates shifting of voltage data for determining difference data, where the voltage data has three threading events, according to certain aspects of the present disclosure.

FIG. 8 illustrates an embodiment of the differencing technique, using the same shift method described in FIG. 7 above, but this time having raw data of a slightly different nature. As shown here, in some embodiments, a threading event may last more than one AC cycle. For example, in the data of FIG. 8, the threading event lasts three cycles, shown by threading events 810, 820, and 830 each occurring during cycles 2, 3, and 4, respectively. However, due to the repeatability in the raw data for each of these threading events, only the first threading event 810 and the last threading event 830 may appear in the processed difference data as positive peak 840 and negative peak 850, respectively. One of ordinary skill will appreciate that peaks 840 and 850 are generally of opposite sign and thus, the positive and negative qualifiers are used herein as merely one example. In addition, the time separation between the positive peak and negative peaks are no longer merely the net time shift applied to the raw data (again, 1 period in this example), but is the sum of the net time shift and the duration of time between first threading event 810 and the last threading event 830.

Figure 9:
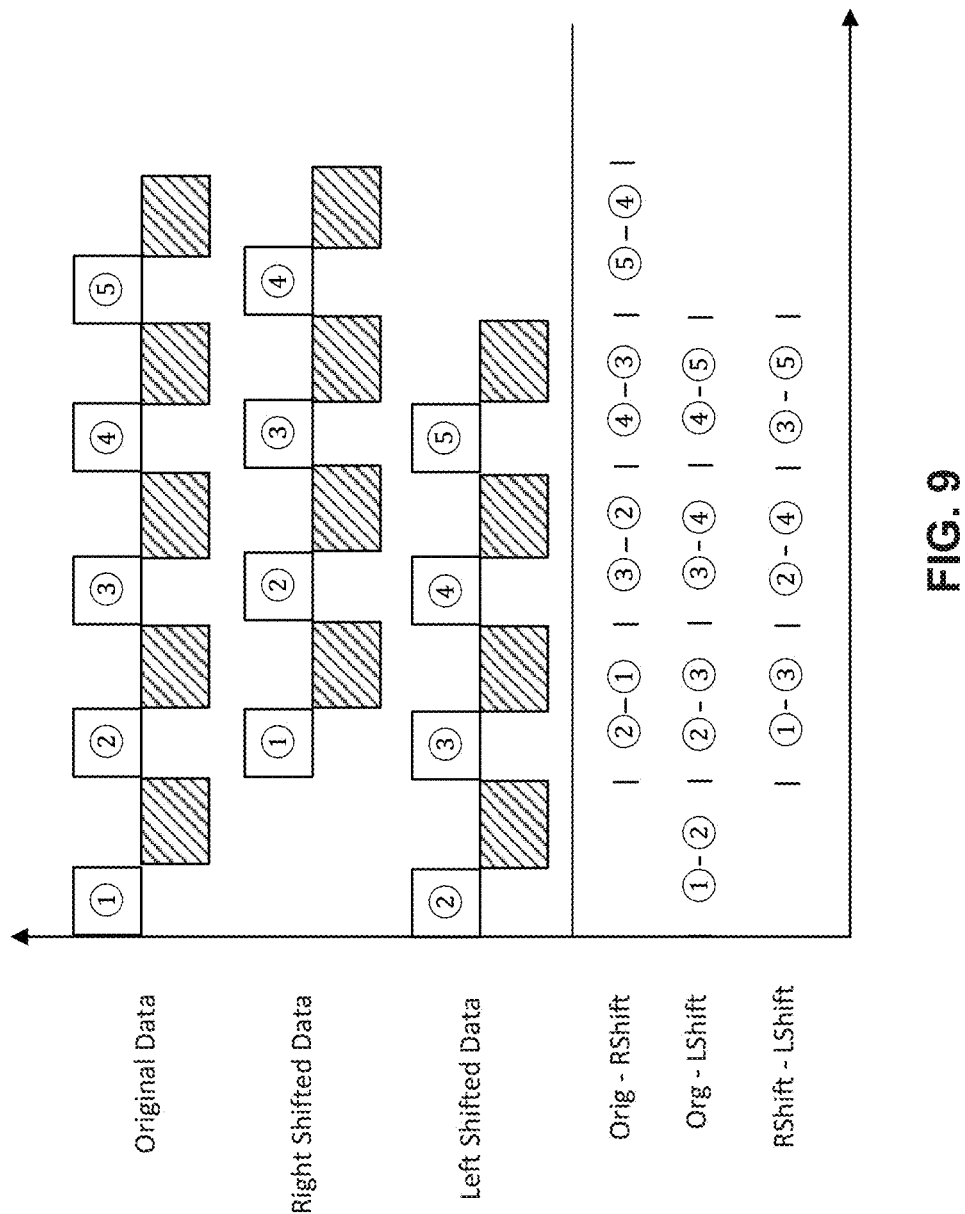
FIG. 9 illustrates a schematic diagram showing examples of time shifts of voltage data, according to certain aspects of the present disclosure.

FIG. 9 shows a schematic diagram to illustrate a method of shifting raw data points for determining difference data according to some embodiments. The first row shows the original data set, with each positive channel marked with a number. The negative channel is not used in this example and is therefore greyed out with diagonal hatching. The second row shows a one cycle right-shift of the data. The third row shows a one cycle left-shift of the data. The fourth row shows an example difference signal, where the difference is the original data minus the right shifted signal, such that the earlier cycle is subtracted from the later cycle.

The fifth row shows the difference data of the original data minus the left shifted signal. In this example, the later cycle is subtracted from the earlier cycle. Thus, a threading event would start with a positive pulse.

The last row shows a difference between the right-shifted data and the left-shifted data. In some embodiments, a nearest neighbor difference (e.g., 1-2) and a second nearest neighbor difference (e.g., 1-3) can be used to determine whether the difference is due to one having a threading event or two having a threading event. In some embodiments, this can help to confirm that two chips provide the same results.

B. Difference Data

Figure 10:
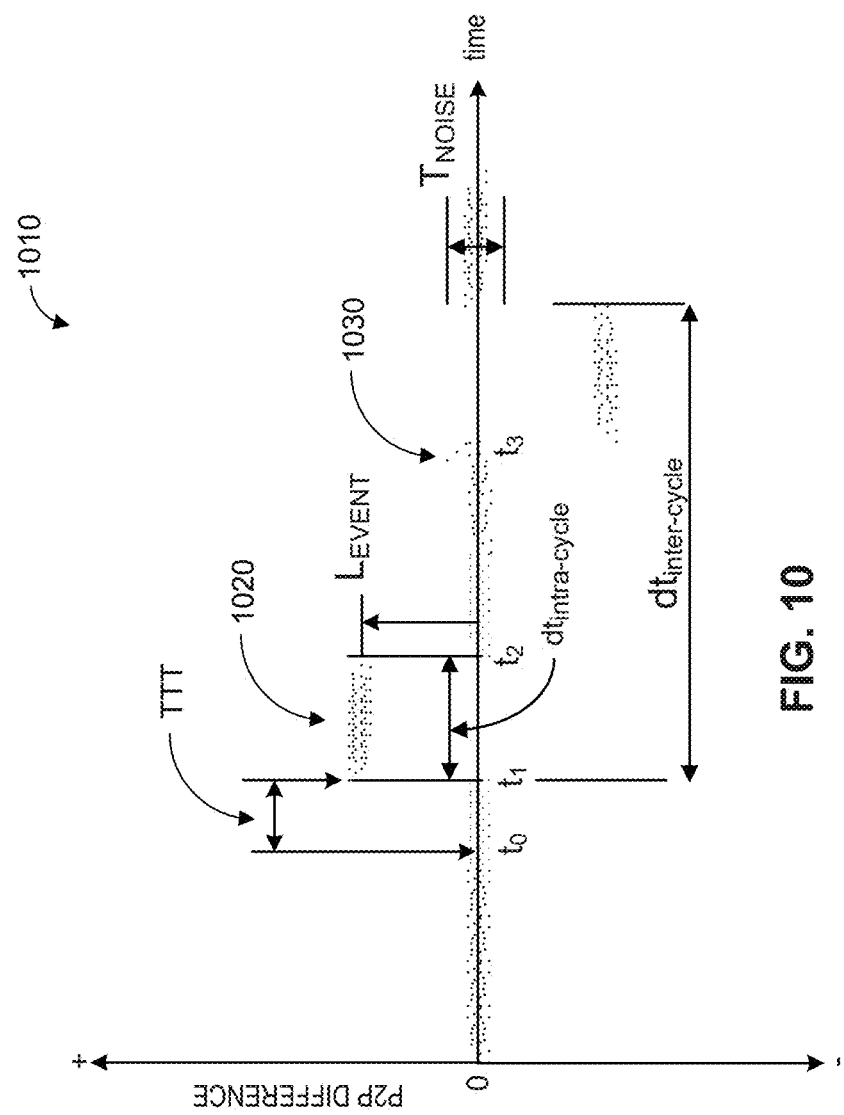
FIG. 10 shows examples of parameters that may be computed from difference data, according to certain aspects of the present disclosure.

FIG. 10 shows an example of difference data for a threading event according to some embodiments. Specifically, FIG. 10 shows a difference data 1010 measured over time as would be produced, e.g., by digital processor 430 during operation of the sequencer. Thus, this embodiment may not have access to the underlying raw AC signals (e.g. the signals shown in FIG. 6). Nevertheless, the information necessary to determine a base call may be extracted from difference data 1010 alone.

As already described above, the positive pulse 1020 represents a threading event that that begins at time $t_1$. In some embodiments, the threading event may occur slightly after the bright mode begins at time $t_0$. For example, as described above in reference to FIG. 5, $t_0$ indicates the moment when $V_{LIQ}$ switches from being smaller than $V_{PRE}$ to being larger than $V_{PRE}$ (or vise versa depending on the architecture of the cell), and thus the precise time at which the direction of the electric field across the pore switched. The time difference $(t_1-t_0)$ provides useful information and, in some embodiments, can be interpreted as the time-to-thread (TTT), i.e., the time it took the tag to be inserted into the nanopore following a dark mode. The TTT can be helpful in design of the system, e.g., in creating nanopore molecules. For example, TTT is a useful design parameter when choosing pores and/or mutating pores for new applications, e.g., to create a new pore with an enhanced (faster) TTT.

In some embodiments, the amplitude $L_{EVENT}$ of the threading pulse (also referred to herein as the "voltage level" or "level") corresponds to a particular tag involved in the threading event, with 4 different (and distinguishable) amplitudes occurring for the open channel (unthreaded channel) and the 4 bases (A, G, C, and T). The width $dt_{intra-cycle}$ of the pulse corresponds to the duration over which the threading event occurred, the so-called "dwell time" (assuming the duration is within a single bright cycle). However, once threaded in first cycle, a tag may typically thread for many cycles after (e.g., 100), and thus the dwell time may extend across many cycles. Accordingly, the dwell time may be more appropriately interpreted to be the intra-cycle dwell time is $dt_{intra-cycle}$. As shown in FIG. 10, the intra-cycle dwell time is $dt_{intra-cycle}$ and can be measured by the width of the first peak in the difference data for a given threading event.

The inter-cycle dwell time is shown as $dt_{inter-cycle}$ and can be measured from the difference data as the time difference from the starting positive pulse and the ending negative pulse, e.g., time difference between first (earliest time) edge of the first pulse and the last edge (latest in time) of the last pulse. Other edges can be used as endpoints without departing from the scope of the present disclosure.

FIG. 8 above discussed a multi-cycle threading event, where the tag threaded on three consecutive cycles. As discussed in FIG. 8, in a multi-cycle threading event, the difference between the voltage points in the middle cycles may typically be zero. However, the subtraction may not be perfect, e.g., TTT for each threading event may differ slightly, leading to a few points between the positive and negative pulses having a level near $L_{EVENT}$. An example of this phenomenon is shown in the sample difference data points 1201 of FIG. 12 below. Such a variation can be distinguished from new threading events based on duration of time because these intra-threading event variations may show up in the data over only one or two ADC cycles. In this manner, the occasional stray point can be assumed to be part of the same threading event signaled by the first large positive pulse.

The peak value of any peaks seen in the data, e.g., noise peak 1030, can be compared to the peak values of the larger threading event pulses to determine whether or not the peaks are noise or a real threading event. As already mentioned above, slow moving changes to the signal, e.g., gain drift from one cycle to another, would likely be consistent from one cycle to another (basically showing up as a DC offset) and can be removed and/or minimized during the differencing process. Thus, the period-to-period differencing method described herein can provide a threading event detector that is generally insensitive to changes that happen at long time scales and/or variations in the data that are repeatable from cycle to cycle. In addition, the baseline of the difference data need not be precisely zero, or even known in advance, because the baseline can be identified from a statistical analysis of the difference data itself, as described below.

In some embodiments, the rate of occurrence of threading events is slow (one or two per second) compared to the sampling rate, e.g., 2 kHz. Accordingly, the zero value can be determined as the most common value (mode) or average value the difference signal. The noise can also be measured (e.g., 1.8 ADC levels) based on, e.g., the variance of the data without threading events (open channel data). The more cells that contribute to the difference signal, the smaller the noise can become, e.g., 1.0 ADC level. Based on the measured noise level, a threshold ($+/-T_{noise}$ shown in FIG. 10) for identifying a threading event can be chosen, e.g., the threshold can be chosen based on the standard deviation of the noise, e.g., only data greater than 6 standard deviations outside the nose may be registered as threading events. Further, the width $dt_{ultra-cycle}$ can be required to be at least a certain number of points, e.g., 3, 4, 5, or 6. Thus, the threading voltage can be required to be seen at least a certain number of times in a cycle, which can reduce noise due to spurious voltage measurements.

C. Calculating Difference Data

Figure 11:
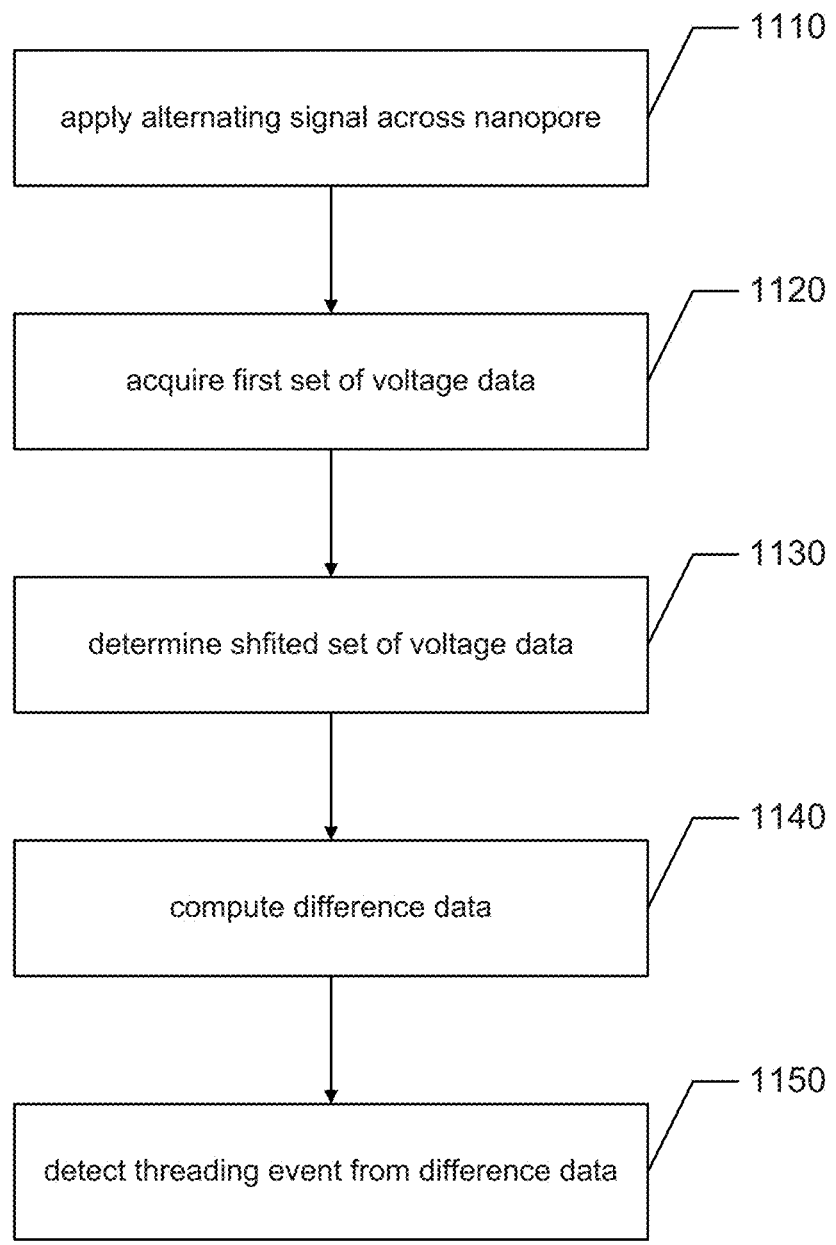
FIG. 11 is a flow chart illustrating an example method of period-to-period analysis of AC signals from nanopore sequencing, according to certain aspects of the present disclosure.

FIG. 11 is a flow chart illustrating an example method of using a sequencing cell, according to certain embodiments. More specifically, FIG. 11 illustrates a method of period-to-period analysis of AC signals from nanopore sequencing according to some embodiments.

In step 1110, an alternating signal (also referred to herein as an "AC signal") is applied across a nanopore of the sequencing cell. Such an AC signal may be a square wave provided by an AC signal generator, similar to AC voltage source 420 (also referred to herein as an AC "signal generator") described above in reference to FIG. 4. In some embodiments, the AC signal may be multiple cycles long with each cycle of the alternating signal comprising a first portion (also referred to herein as the "bright mode" or "bright period") and a second portion (also referred to herein as the "dark mode" or "dark period"). The voltage levels of the second portion are opposite of a reference voltage than a voltage levels of the first portion ($V_{LIQ}$ is either above or below $V_{PRE}$ in the embodiment shown in FIG. 5). As described above in reference to FIGS. 1-2, in some embodiments, the nanopore is configured to receive a tag that is connected to a nucleotide thereby creating a threading event.

In step 1120, a first set of voltage data (also referred to herein as "unshifted voltage data" or "raw voltage data") is acquired, e.g., by ADC 410, as described above in reference to FIG. 4. In some embodiments, the first set of voltage data is acquired during the first portion (e.g., the bright period) of the multiple cycles of the alternating signal. Examples of the first set of voltage data include the data points shown in bright period 520 of FIG. 5 and also all points characterized as within a "B" period, as shown in FIGS. 7-8. As shown in FIG. 7-8, the first set of voltage data can include voltage data points acquired over multiple cycles of the AC signal. As described above, voltage data corresponds to (i.e. depends on) a value of a resistance of the nanopore at a different time, where the resistance of the nanopore changes when the tag is received within the nanopore.

In step 1130, a time-shifted set of voltage data is determine from the acquired raw voltage data e.g., by digital processor 430 shown above in FIG. 4. Examples of shifted data are shown in FIGS. 7-9, as discussed above. In some embodiments, each cycle of data points of the raw set of voltage data and the shifted set of voltage data includes a specified number of data points, the raw unshifted data may include 15 data points within a bright period and the shifted data may include a corresponding 15 data points within a bright period. Because the shifted data is time-shifted relative to the unshifted data the data points of the shifted data and the data points of the unshifted data are from different cycles of the AC signal, as discussed above, e.g. in reference to FIGS. 7-9 above. For example, turning briefly to FIG. 9, the unshifted data points may originate from cycle 1 of the unshifted data and the shifted data points may originate from unshifted cycle 2 as shown in the example labeled Org-LShift.

In step 1140, difference data is computed, e.g., by digital processor 430 shown above in FIG. 4, by computing differences between data points of the unshifted set of voltage data and corresponding data points of the shifted set of voltage data. In some examples, the corresponding data points have the same position in a respective cycle but may be present in different cycles. For example, for unshifted data points that originate from cycle 1 of the unshifted data and shifted data points originate from cycle 2 of the unshifted data, difference data may be computed in the following manner: the first difference data point may be computed by subtracting the first point from cycle 1 from the first point of cycle two, the second difference data point may be computed by subtracting the second point from cycle 1 from the second point of cycle 2, and so on. One of ordinary skill having the benefit of this disclosure will appreciate that there are many different ways to perform the difference, and the single point method described above is meant as merely one example among many. For example, multiple data points from each cycle may be averaged or filtered before subtraction or differences may be computed based on nearest neighbor subtractions, next nearest neighbor subtractions or the like without departing form the scope of the present disclosure.

In step 1150, a threading event is detected (i.e., a tag has been received within the nanopore) based on one or more data points in the difference data. For example, a threading event may be identified by the presence of a pulse in the difference data as described above in reference to FIG. 10. In some embodiments, threading events are determined by identifying an open channel level as the mode of the difference data. Threading events may be identified by determining a starting pulse of the difference data exceeds a threshold value, determining an ending pulse in the difference data that follows the starting pulse and is of an opposite sign from a sign of the starting pulse, and determining a time difference between the starting pulse and the ending pulse. In some embodiments, the threshold value may be determined from the mode of the difference data, as described above in reference to FIG. 10.

In some embodiments, for a given cell, the unshifted data (i.e. the raw data) can effectively be copied and the copy stored in memory. The difference between the corresponding voltage points of neighboring cycles is then computed using the stored unshifted data and the stored copy of the unshifted data or a time-shifted copy of the unshifted data. Equivalently, a single copy of the unshifted data can be used with the points of a current pair of cycles being read by a processor with a difference taken between the two.

In the data processor cache, there can be stored locations, with a given cycle stored in one location and used for every two cycles. For one calculation, the cycle data points would correspond to the initial cycle for determining the difference. For a next calculation, the cycle data points would correspond to the ending cycle for determining the difference. In this manner, the number of operations can be reduced relative to having two copies of the entire array and reading two sets of cycle data points for every difference calculation.

For example, a first set of data points can be stored in a first memory location and a second set of data points can be stored in a second memory location. A difference can be taken of the set of data points at the first memory location minus the set of data points at the second memory location. Then, for next calculation, the first set of data points can be removed from memory, a third set of data points can be stored in the first memory location. The next difference taken will be of the second set of data points at the second memory location minus the third set of data points at the first memory location and so on.

While the above differencing method is described in the context of a digital signal processing technique, the present disclosure is not so limited. For example, analog techniques may be employed instead of, or in combination with, digital techniques without departing from the scope of the present disclosure. For example, the time shifting and differencing computation may be performed by one or more analog circuit elements, e.g. phase shifters, operational amplifiers, analog filters, or the like.

D. Data Compression and Performance

Computation of several properties of the pulses can allow compression of data, since the physical information needed for base calling may be extracted from a small set of properties of the pulses, with this set of properties being stored as a few parameters in memory. Chips can be large, e.g., hundreds of thousands of cells or even millions, at a sampling rate of 2 kHz. Thus, in the case where every voltage point is stored, terabytes of data can be produced and associated storage costs can be high. In some embodiments, data compression through the computation of threading event parameters based on difference data can use only a handful of parameters to be stored per threading event, thereby greatly reducing storage requirements and cost.

Examples of the parameters stored for a threading event can include the one or more level(s) $L_{EVENT}$, the time to thread TTT, and the various time differences, e.g., the time difference between the starting pulse and the ending pulse. As described above in reference to FIG. 10, the intra-cycle dwell time and inter-cycle dwell time can be computed and stored as compressed data.

In some embodiments, the difference data processed by the method disclosed herein includes a few other beneficial features. First, all non-threaded (i.e., open channel) data has a low amplitude, with open channel values for the difference data clustered around zero (or around some offset). On the other hand, threading events appear as abrupt steps (also referred to herein as pulses and/or peaks) whose amplitudes rise above the background noise level, e.g., event peak 750 shown in FIG. 7. This leads to the possibility for data compression. In some embodiments, and as discussed in further detail above in reference to FIGS. 10-11, to compress the data, only the minimum data necessary to characterize the peaks can be stored, with all other data being discarded. Second, because long term systematic drifts in the data (such as gain drift and/or offset shift) occur with a similar magnitude for two cycles that are relatively close in time, subtracting data from different cycles, as done here, corrects the data by removing these types of systematic effects. More generally, the processed data can be relatively immune to any systematic shifts in the data that 1) occur on a timescale that is long compared to the AC period; and/or 2) that occur in a repeatable manner from cycle to cycle.

Another benefit of the method disclosed herein relates to improved processing speed. Since the proposed method is based on differences in ADC values (1-byte data), it is fast if data is properly memory aligned. In addition, it can be easily vectorized per cell and parallelized for multiple cells. A throughput on the order of 100 MB/s can be expected for a single processor doing analysis on ubf files. In principle, one can skip ubf files by having data directly accessible (e.g., in a ring buffer) for processing. Thus, some embodiments of the method and system may be used for real-time processing, e.g., using FPGA. Employment of the method disclosed herein can also obviate need of using intermediate formats like hdf5 for processing. In addition, since the method is naturally adaptive and based on local neighborhood it may not require extensive background processing.

IV. Results

FIGS. 12-14 show raw sequencing data and processed difference data according to some embodiments.

Figure 12A:
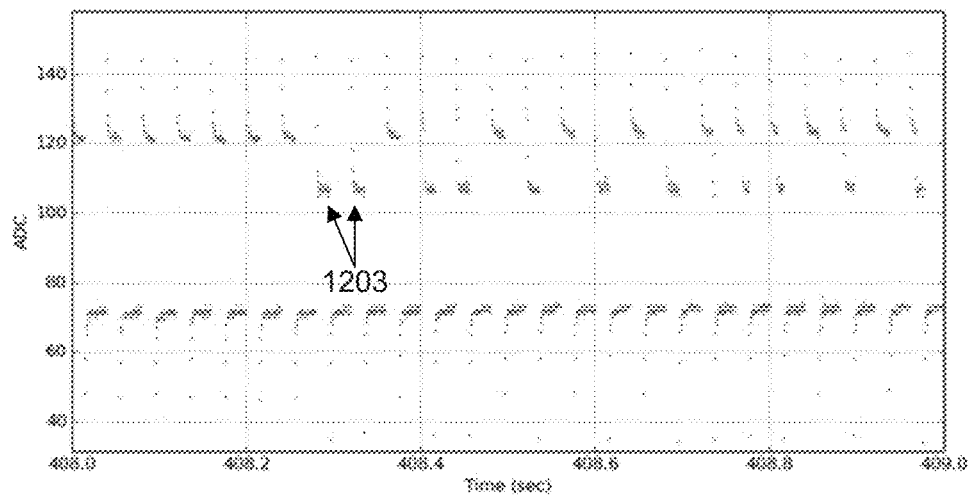
FIGS. 12A and 12B show sample data showing a comparison of processed difference data and raw-ADC data showing events, according to certain aspects of the present disclosure.

FIG. 12A shows a relatively short timescale (1 s total duration) plot of raw ADC test data showing individual AC cycles along with enough resolution to show individual bright and dark periods within each AC cycle. Several of the bright periods show threading events, e.g., threading events 1203. Each of the threading events has approximately the same ADC level, approximately 110, indicating that the same tag is being threaded into the nanopore in each event. There are several reasons why this may occur, e.g., it may take several cycles to catalyze the base associated with the tag or multiple tagged bases of the same type may repeat in the nucleic acid being sequenced.

Figure 12B:
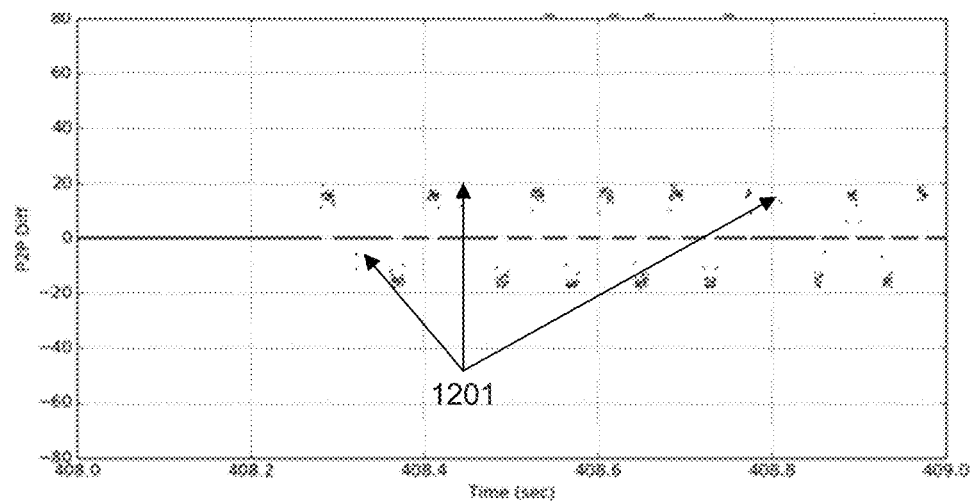

FIG. 12B shows difference data (p2p_diff) that has been computed from the raw (unshifted) ADC data shown in FIG. 12A, according to some embodiments. As described above in reference to FIGS. 6-9, in the difference data, each threading event is represented by a pair of event pulses having opposite signs. In addition, for multi-cycle threading events, the differencing process may not be perfect, e.g., if the TTT varies slightly from cycle to cycle, as discussed above in reference to FIG. 10. In this case, a few sample difference data points 1201 between the positive and negative pulses have a level that is comparable to the threading amplitude. However, these stray data points can be differentiated from threading events based on the timescales involved, i.e., they are much faster than real threading events.

Figure 13A:
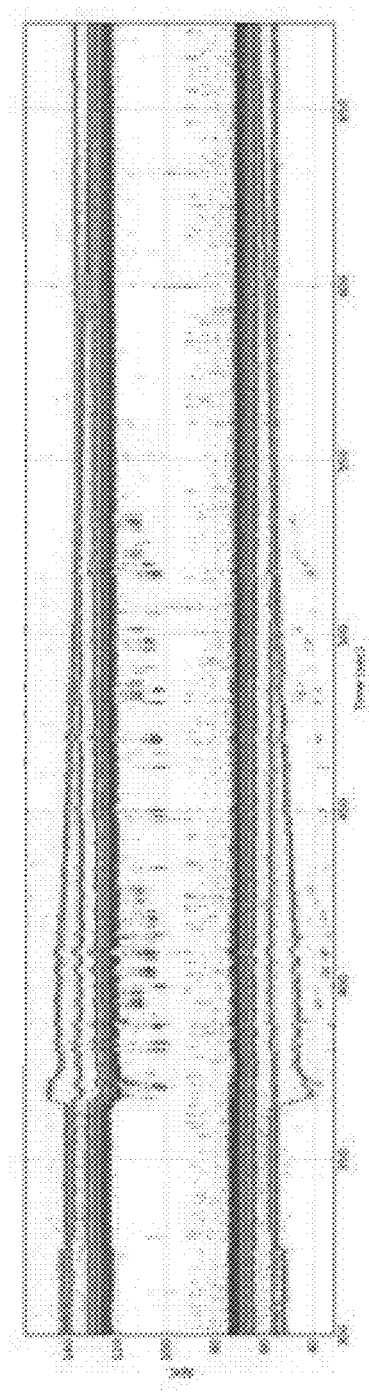
FIGS. 13A and 13B show sample data showing a comparison of processed signals from the proposed method and raw-ADC signals showing threading events, according to certain aspects of the present disclosure.
Figure 13B:
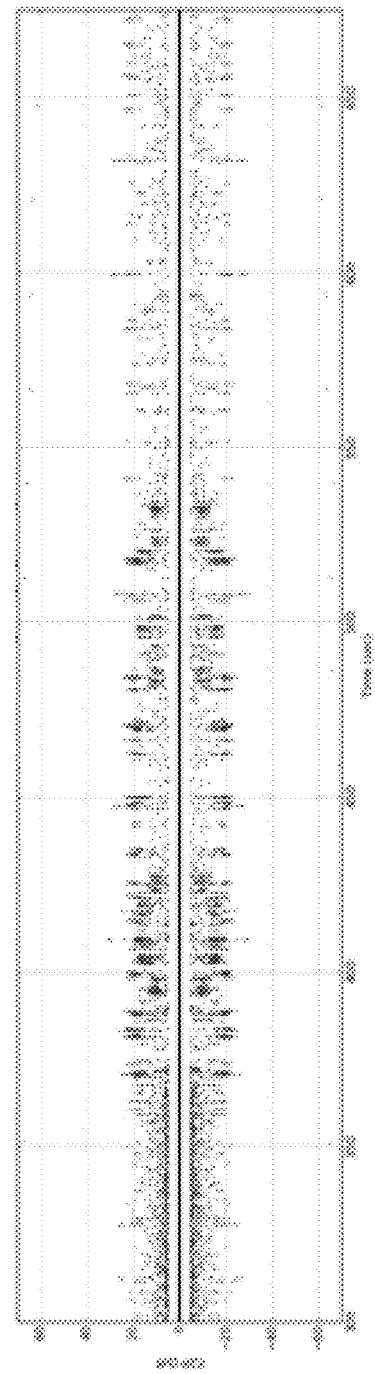

FIGS. 13A and 13B show the results of the period-to-period differencing method, according to some embodiments. FIGS. 13A and 13B show raw ADC data and processed difference data over a duration of about 150 s and thus many more threading events can be seen as compared to FIGS. 12A and 12B. Furthermore, the raw ADC data shown in FIG. 13A also evidences a time-varying gain drift in both the bright mode and dark mode data. This drift leads to the unprocessed data being error prone. However, as shown in FIG. 13B, because the drift is relatively stable from cycle to cycle (individual cycles are too fast to be seen here) the drift is effectively removed in the difference data. Furthermore, the difference data in FIG. 13B that is below a threshold value is deemed to be noise and is removed. FIG. 13B thus demonstrates that this data is not necessary to detect the threading events and can be removed to reduce overall data storage requirements.

Figure 14A:
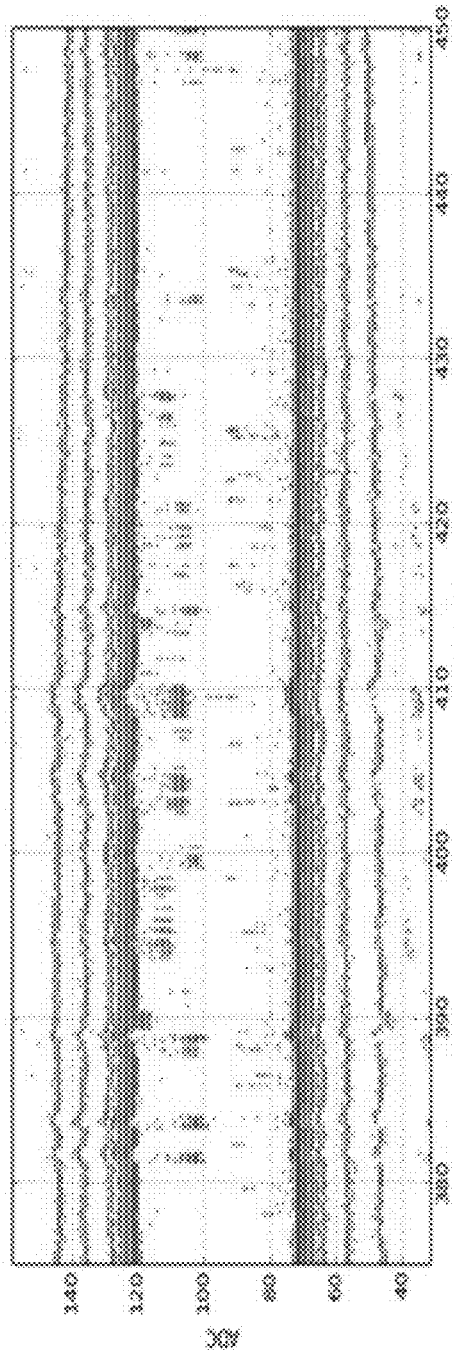
FIGS. 14A and 14B show sample data showing a comparison of processed signals from the proposed method and raw-ADC signals showing threading events, according to certain aspects of the present disclosure.
Figure 14B:
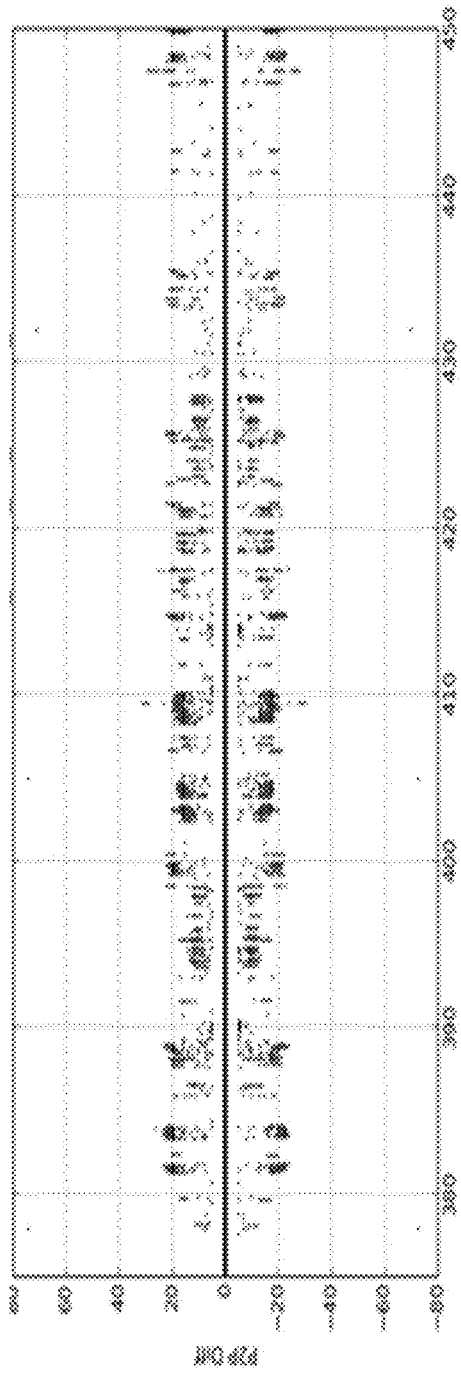

FIGS. 14A and 14B show another set of sample data that is data similar to that shown in FIGS. 13A and 13B. In the raw ADC data shown in FIG. 14A, a phenomena known as baseline shift is observed. In some embodiments, this phenomena may be caused by a cell's charge balance being abruptly brought out of equilibrium each time a threading event occurs. As a result, during a threading event, both the bright mode and the dark mode data trend upwards, and then begin to trend back downwards over time as the charges on capacitive elements in the cell redistribute to reach an equilibrium state. FIG. 14B shows that the differencing method disclosed herein is able to effectively correct for this offset shift. As in FIGS. 13A-13B, the difference data below a certain threshold is removed to reduce overall data storage requirements.

In some embodiments, the difference data can be used to conduct a preliminary analysis of the data to identify threading events. Later processing can involve classifying of events as a particular base call and then alignment. Accordingly, embodiments can obtain a signal from one or more sequencing cells, detect events, classify events to form basecalls, put bases in a sequence, and align to a reference genome.

Some experimental parameters of the system can be amount of salt, type of salt, amount of voltage at pore, type of nanopore, duty cycle of bright and dark modes, and frequency of AC signal and data acquisition rate. Embodiments can be agnostic to these different experimental parameters. Other benefits are speed of operation, ability to program into simple hardware (e.g., FPGA as opposed to GPU, or on basic CPU), and data reduction (less memory).

V. Computer System

Figure 15:
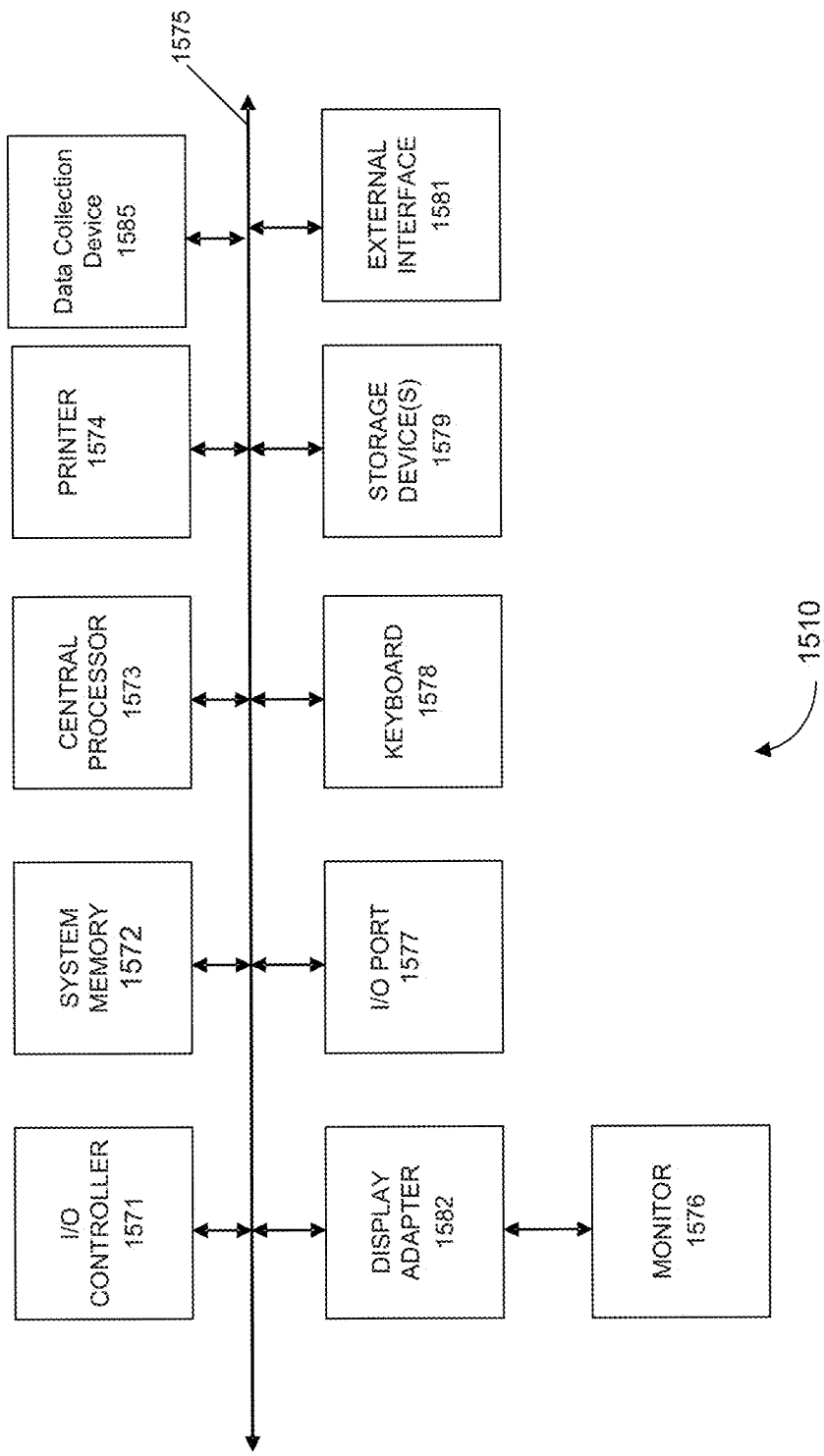
FIG. 15 shows a block diagram of an example computer system usable with systems and methods, according to certain aspects of the present disclosure.

Any of the computer systems mentioned herein may utilize any suitable number of subsystems. Examples of such subsystems are shown in FIG. 15 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 15 are interconnected via a system bus 1575. Additional subsystems such as a printer 1574, keyboard 1578, storage device(s) 1579, monitor 1576, which is coupled to display adapter 1582, and others are shown. Peripherals and input/output (I/O) devices, which couple to I/O controller 1571, can be connected to the computer system by any number of means known in the art such as input/output (I/O) port 1577 (e.g., USB, FireWire®). For example, I/O port 1577 or external interface 81 (e.g. Ethernet, Wi-Fi, etc.) can be used to connect computer system 1510 to a wide area network such as the Internet, a mouse input device, or a scanner. The interconnection via system bus 1575 allows the central processor 1573 to communicate with each subsystem and to control the execution of a plurality of instructions from system memory 1572 or the storage device(s) 1579 (e.g., a fixed disk, such as a hard drive, or optical disk), as well as the exchange of information between subsystems. The system memory 1572 and/or the storage device(s) 1579 may embody a computer readable medium. Another subsystem is a data collection device 1585, such as a camera, microphone, accelerometer, and the like. Any of the data mentioned herein can be output from one component to another component and can be output to the user.

A computer system can include a plurality of the same components or subsystems, e.g., connected together by external interface 1581 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated.

All patents, patent applications, publications, and descriptions mentioned herein are incorporated by reference in their entirety for all purposes. None is admitted to be prior art.

What is claimed is:

1. A system comprising:
   a sequencing cell that includes a nanopore, the nanopore configured to receive a tag that is connected to a nucleotide, thereby creating a threading event;
   a signal generator configured to apply an alternating signal across the nanopore of the sequencing cell, the alternating signal comprising cycles, each of the cycles of the alternating signal comprising a first portion and a second portion, wherein voltage levels of the second portion are opposite of a reference voltage than voltage levels of the first portion;
   an analog-to-digital converter configured to acquire a first set of voltage data during the first portion of a plurality of the cycles of the alternating signal, the voltage data comprising data points, wherein each of the data points of the first set of voltage data corresponds to a value of a resistance of the nanopore at a different time, where the resistance of the nanopore changes when the tag is received within the nanopore; and
   a digital processor configured to:
      determine a time-shifted set of voltage data from the first set of voltage data, wherein each cycle of data points of the first set of voltage data and the time-shifted set of voltage data includes a specified number of data points;
      compute difference data by computing differences between the data points of the first set of voltage data and corresponding data points of the time-shifted set of voltage data; and
      identify the threading event based on one or more data points in the difference data.

2. The system of claim 1, further comprising a switch configured to selectably apply a voltage across the nanopore, wherein the switch is configured to open and close a plurality of times during the first portion of the alternating signal.

3. The system of claim 1, wherein the time-shifted set of voltage data comprises data points selected from stored data representing the first set of voltage data.

4. The system of claim 3, wherein the data points of the time-shifted set of voltage data are selected from a time-shifted copy of the first set of voltage data, and wherein computing the difference data further comprises computing a difference between corresponding data points of the first set of voltage data and the time-shifted copy of the first set of voltage data.

5. The system of claim 1, wherein the digital processor is further configured to determine the time-shifted set of voltage data by:
   selecting a first subset of the first set of voltage data; and
   selecting a second subset of the first set of voltage data, wherein the cycles of the second subset of the first set of voltage data are different cycles from the cycles of the first subset of the first set of voltage data.

6. The system of claim 5, wherein the corresponding data points are selected from the first subset of the first set of voltage data and from the second subset of the first set of voltage data.

7. The system of claim 1, wherein the digital processor is further configured to determine the time-shifted set of voltage data by:
   generating a copy of the first set of voltage data;
   generating the time-shifted set of voltage data by applying a time shift to the copy of the first set of voltage data; and
   storing both the first set of voltage data and the time-shifted set of voltage data in memory.

8. The system of claim 1, wherein the digital processor is further configured to:
   identify a mode of the difference data;
   determine a starting pulse of the difference data that exceeds a threshold value, wherein the threshold value is determined from the mode;
   determine an ending pulse in the difference data that follows the starting pulse and is of an opposite sign;
   determine a time difference between the starting pulse and the ending pulse; and
   store the time difference and an amplitude of the starting pulse and/or ending pulse in memory.

9. The system of claim 1, further comprising:
   a sequencing chip that includes a plurality of sequencing cells, wherein the digital processor is further configured to:
   analyze a plurality of sets of difference data, wherein each one of the plurality of sets of difference data comes from a respective one of the plurality of sequencing cells.

10. The system of claim 9, wherein the digital processor is further configured to cluster values of the plurality of sets of difference data to determine cutoff values for determining a base call based on levels of pulses in the difference data.

11. A method of using a sequencing cell, the method comprising:
   applying an alternating signal across a nanopore of the sequencing cell, the nanopore configured to receive a tag that is connected to a nucleotide, thereby creating a threading event, the alternating signal comprising cycles, each cycle of the alternating signal comprising a first portion and a second portion, wherein voltage levels of the second portion are opposite of a reference voltage than voltage levels of the first portion;
   acquiring a first set of voltage data during the first portion of a plurality of the cycles of the alternating signal, wherein each data point of the first set of voltage data corresponds to a value of a resistance of the nanopore at a different time, where the resistance of the nanopore changes when the tag is received within the nanopore;
   determining a time-shifted set of voltage data from the first set of voltage data, wherein each cycle of data points of the first set of voltage data and the time-shifted set of voltage data includes a specified number of data points;
   computing difference data by computing differences between the data points of the first set of voltage data and corresponding data points of the time-shifted set of voltage data; and
   identifying the threading event based on one or more data points in the difference data.

12. The method of claim 11, wherein the corresponding data points have a same position in different cycles.

13. The method of claim 11, wherein the corresponding data points of the time-shifted set of voltage data are selected from the first set of voltage data, wherein the data points of the shifted data are selected from different cycles than the cycles for the specified number of data points.

14. The method of claim 11, wherein the time-shifted set of voltage data comprises data points selected from a time-shifted copy of the first set of voltage data, and wherein computing the difference data:
   comprises computing a difference between corresponding data points of the first set of voltage data and the time-shifted copy of the first set of voltage data.

15. The method of claim 11, wherein determining the time-shifted set of voltage data further comprises:
   selecting a first subset of the first set of voltage data; and
   selecting a second subset of the first set of voltage data, wherein the cycles of the second subset of the first set of voltage data are different cycles from the cycles of the first subset of the first set of voltage data.

16. The method of claim 15, wherein the corresponding data points are selected from the first subset of the first set of voltage data and from the second subset of the first set of voltage data.

17. The method of claim 11, wherein determining the time-shifted set of voltage data further comprises:
   generating a copy of the first set of voltage data;
   generating the time-shifted set of voltage data by applying a time shift to the copy of the first set of voltage data; and
   storing both the first set of voltage data and the time-shifted set of voltage data in memory.

18. The method of claim 11, further comprising:
   identifying a mode of the difference data; and
   determining a starting pulse of the difference data that exceeds a threshold value, wherein the threshold value is determined from the mode.

19. The method of claim 18, further comprising:
   determining an ending pulse in the difference data that follows the starting pulse and is of an opposite sign from a sign of the starting pulse;
   determining a time difference between the starting pulse and the ending pulse; and
   store the time difference and an amplitude of the starting pulse and/or ending pulse in memory.

20. The method of claim 11, further comprising:
   analyzing a plurality of sets of difference data, wherein each one of the plurality of sets of difference data comes from a respective one of a plurality of sequencing cells of a sequencing chip; and
   clustering a plurality of values of the plurality of sets of difference data to determine cutoff values for determining a base call based on levels of pulses in the difference data.

21. A non-transitory computer-readable storage medium storing computer-executable instructions that, when executed by a processor, cause a sequencing cell to perform operations comprising:
   applying an alternating signal across a nanopore of the sequencing cell, the nanopore configured to receive a tag that is connected to a nucleotide, thereby creating a threading event, the alternating signal comprising cycles, each cycle of the alternating signal comprising a first portion and a second portion, wherein a voltage level of the second portion is opposite of a reference voltage than a voltage level of the first portion;
   acquiring a first set of voltage data during the first portion of a plurality of the cycles of the alternating signal, wherein each data point of the first set of voltage data corresponds to a value of a resistance of the nanopore at a different time, where the resistance of the nanopore changes when the tag is received within the nanopore;
   determining a time-shifted set of voltage data from the first set of voltage data, wherein each cycle of data points of the first set of voltage data and the time-shifted set of voltage data includes a specified number of data points;
   computing difference data by computing differences between the data points of the first set of voltage data and corresponding data points of the time-shifted set of voltage data; and
   identifying the threading event based on one or more data points in the difference data.

* * * * *